(12) United States Patent
Piston et al.

(10) Patent No.: US 8,031,338 B2
(45) Date of Patent: Oct. 4, 2011

(54) MEASURING FORSTER RESONANCE ENERGY TRANSFER WITH POLARIZED AND DEPOLARIZED LIGHT

(75) Inventors: David Piston, Nashville, TN (US); Mark Rizzo, Nottingham, MD (US)

(73) Assignee: Vanderbilt University, Nashville, TN (US)

( * ) Notice: Subject to any disclaimer, the term of this patent is extended or adjusted under 35 U.S.C. 154(b) by 1676 days.

(21) Appl. No.: 11/291,111

(22) Filed: Nov. 30, 2005

(65) Prior Publication Data

US 2006/0160111 A1     Jul. 20, 2006

Related U.S. Application Data

(60) Provisional application No. 60/632,668, filed on Dec. 2, 2004.

(51) Int. Cl.
    *G01J 3/447* (2006.01)
(52) U.S. Cl. ...................................................... 356/327
(58) Field of Classification Search ........................ None
    See application file for complete search history.

(56) References Cited

U.S. PATENT DOCUMENTS

| | | | | |
|---|---|---|---|---|
| 6,500,650 | B1 * | 12/2002 | Stanton et al. ................ | 435/91.1 |
| 6,803,201 | B2 * | 10/2004 | Sorge et al. ........................ | 435/6 |
| 6,821,750 | B2 * | 11/2004 | Hobbs et al. ................. | 435/69.1 |
| 6,972,198 | B2 * | 12/2005 | Craig et al. .................... | 436/164 |
| 7,033,810 | B2 * | 4/2006 | Tian et al. ..................... | 435/196 |
| 7,183,066 | B2 * | 2/2007 | Fernandez-Salas et al. . | 435/7.32 |
| 2002/0152479 | A1 * | 10/2002 | Lehmann et al. ................. | 800/3 |
| 2003/0003520 | A1 * | 1/2003 | Shan et al. .................... | 435/7.21 |
| 2003/0228703 | A1 | 12/2003 | Hoppe et al. ................... | 436/172 |
| 2005/0095174 | A1 * | 5/2005 | Wolf .......................... | 422/82.08 |
| 2005/0227306 | A1 * | 10/2005 | Fox et al. ........................ | 435/23 |
| 2006/0141531 | A1 * | 6/2006 | Ebright et al. ................. | 435/7.1 |
| 2009/0294691 | A1 * | 12/2009 | Trinquet et al. ............ | 250/459.1 |

FOREIGN PATENT DOCUMENTS

| | | |
|---|---|---|
| EP | 1571448 | 9/2005 |
| WO | WO 2004/053499 | 6/2004 |
| WO | WO 2005/026730 | 3/2005 |
| WO | WO 2006/010839 | 2/2006 |

OTHER PUBLICATIONS

Moens et al., "Detection of Tryptophan to Tryptophan Energy Transfer in Proteins", The Protein Journal, vol. 23, No. 1, Jan. 2004.*

Chiu et al., "Ras signalling on the endoplasmic reticulum and the golgi," *Nat. Cell. Biol*,. 4(5):343-350, 2002.
Jares-Erijman and Jovin, "Fret Imaging,," *Nat. Biotechnol.*, 21:1387-1395, 2003.
Karasawa et al., "Cyan-emitting and orange emitting fluorescent proteins as a donor/acceptor pair for fluorescence resonance energy transfer," *Biochem J.*, 381:307-312, 2004.
Mattheyses et al., "Polarized fluorescence resonance energy transfer microscopy," Biophys J., 87:2787-2797, 2004.
Miyawaki, "Visualization of the spatial and temporal dynamics of intracellular signaling," *Dev. Cell.*, 4:295-305, 2003.
Nagai et al., "A variant of yellow fluorescent protein with fast and efficient maturation for cell-biological applications," *Nat. Biotechnol.*, 20(1):87-90, 2002.
Prasher et al., "Primary structure of the aequorea victoria green-fluorescent protein," *Gene*, 111:229-233, 1992.
Rizzo and Piston, "High-contrast imaging of fluorescent protein fret by fluorescence polarization microscopy," *J. Biophys.*, 88:L14-L16, 2005.
Rizzo et al., "An improved cyan fluorescent protein variant useful for fret," *Nat. Biotechnol.*, 22(4):445-449, 2004.
Tsien, "The green fluorescent protein," *Ann. Rev. Biochem.*, 67:509-544, 1998.
Zacharias et al. "Partitioning of lipid-modified monomeric gfps into membrane microdomains of live cells," *Science*, 296(5569):913-916, 2002.
Cohen-Kashi et al., "Fluorescence resonance energy transfers measurements on cell surfaces via fluorescence polarization," *Biophysical Journal*, 82:1395-1402, 2002.
Moens et al., "Detection of tryptophan to tryptophan energy transfer in proteins," *Protein Journal*, 23:79-83, 2004.
Jameson et al., "Intrinsic fluorescence of elongation factor Tu in its complexes with GDP and elongation factor Ts," *Biochemistry*, 26:3894-3901, 1987.
Jares-Erijman and Jovin, "FRET imaging," *Nature Biotech.*, 21:1387-95, 2003.
Mitra et al., "Fluorescence resonance energy transfer between blue-emitting and red-shifted excitation derivatives of the green fluorescent protein," *Gene*, 173:13-7, 1996.
Weber, "Fluorescence-polarization spectrum and electronic-energy transfer in tyrosine, tryptophan and related compounds," *Biochem. J.*, 75:335-345, 1960.
Weber, "Fluorescence-polarization spectrum and electronic-energy transfer in proteins," *Biochem. J.*, 75: 345-352, 1960.

* cited by examiner

*Primary Examiner* — Ann Lam
(74) *Attorney, Agent, or Firm* — Fulbright & Jaworski

(57) ABSTRACT

The present invention provides improved methods for assessing Förster resonance energy transfer using polarized light. Specifically, the methods rely on measuring depolarized light emitted by fluorescent acceptor molecules.

11 Claims, 5 Drawing Sheets

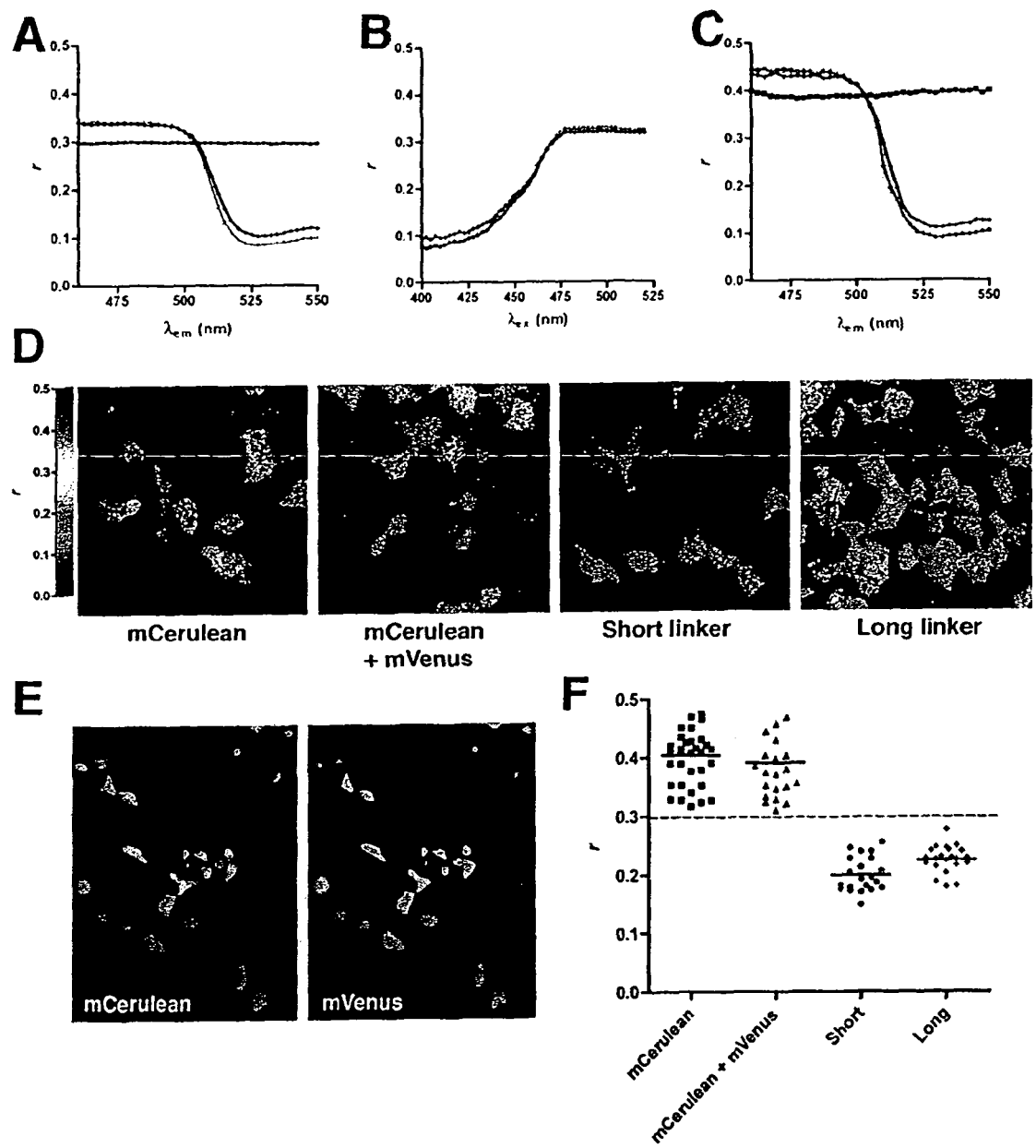
FIGS. 3A-F

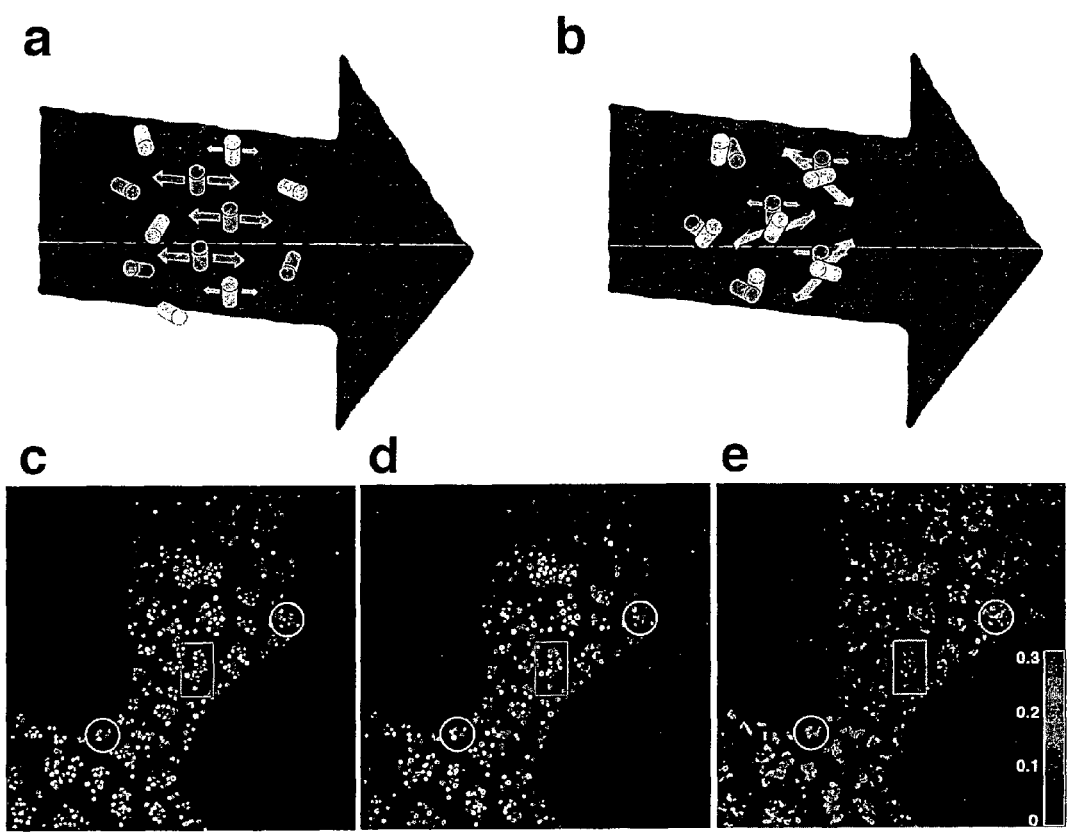
FIG. 4A-E

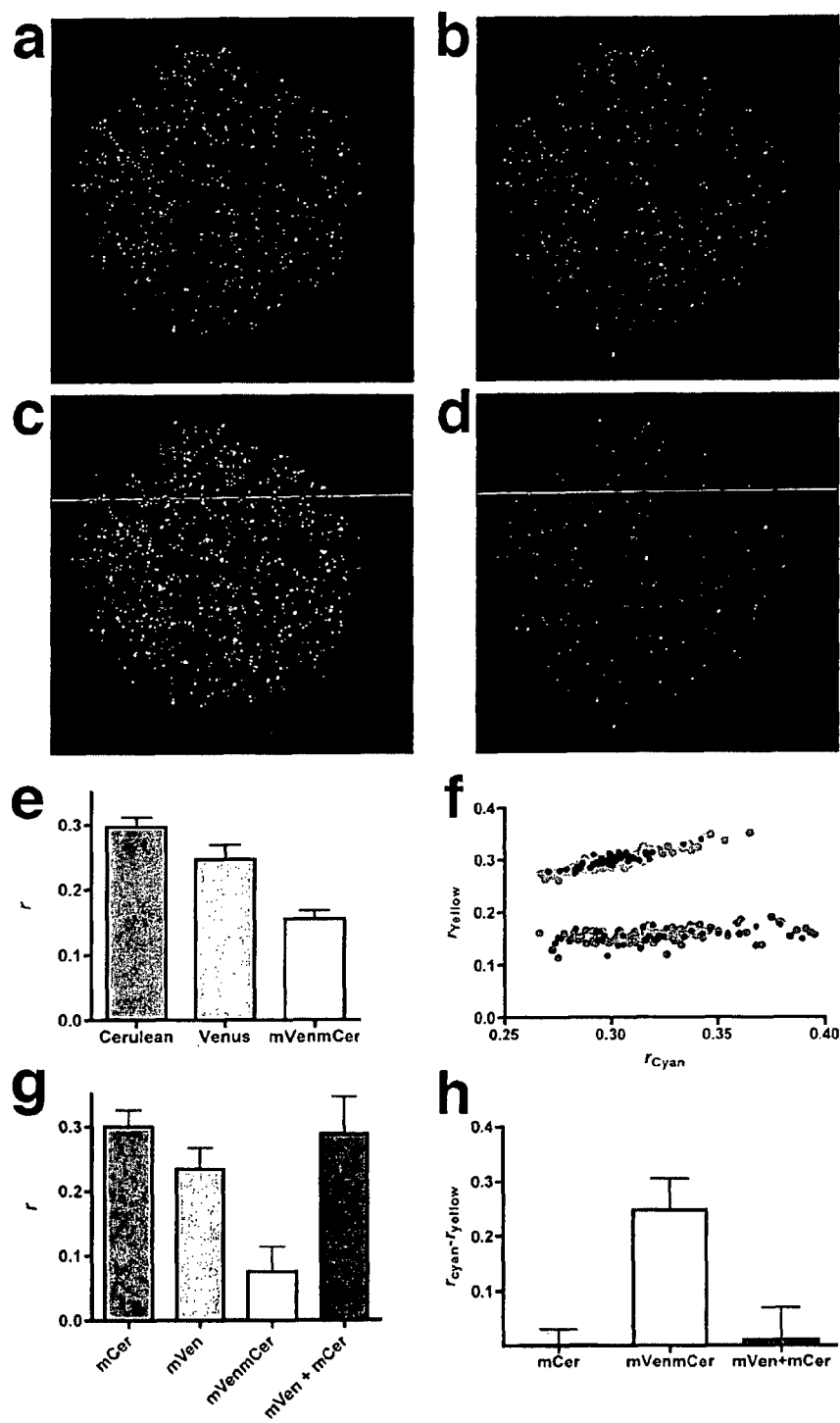
FIG. 5A-H

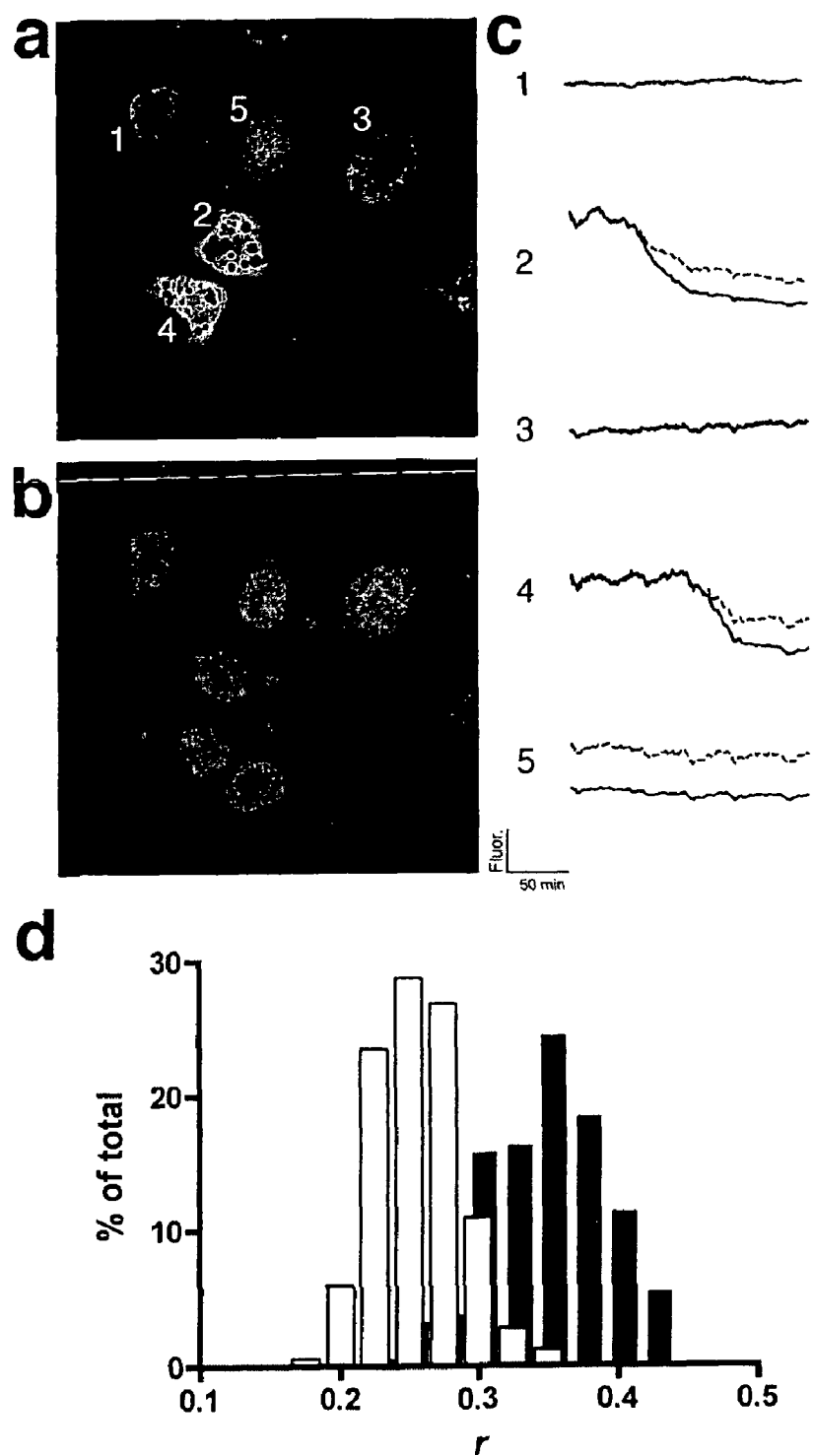
FIG. 6A-D

__US 8,031,338 B2__

MEASURING FORSTER RESONANCE ENERGY TRANSFER WITH POLARIZED AND DEPOLARIZED LIGHT

The present invention claims benefit of priority to U.S. Provisional Application Ser. No. 60/632,668, filed Dec. 2, 2004, the entire contents of which are hereby incorporated by reference.

The government owns rights in the present invention pursuant to grants numbered DK053434 and GM072048 from the National Institutes of Health, grant number BBI-9871063 from the National Science Foundation, and grant number FA9550-04-1-0455 from the Department of Defense.

BACKGROUND OF THE INVENTION

1. Field of the Invention

The present invention relates generally to the fields of protein biochemistry and fluorescence (Förster) resonance energy transfer. More specifically, the invention relates to the use of polarized/depolarized light to measure FRET.

2. Description of Related Art

Measurement of intracellular processes and protein-protein interactions in living cells relies extensively on green fluorescent protein-based bioassays. Many of these assays incorporate measurement of Förster resonance energy transfer (FRET) between different colors of fluorescent proteins, most commonly, the cyan (CFP) and yellow fluorescent proteins (YFP) (Miyawaki, 2003). Given the inherent sensitivity of FRET measurements to distance and orientation (Förster, 1948; Clegg, 1992), the changes in energy transfer are difficult to measure between FRET partners with broadly overlapping spectra, such as fluorescent proteins. Crosstalk excitation of the donor YFPs also leads to "false positive" indication of FRET, and serves as a barrier for adaptation of CFP:YFP based assays to high throughput assays. Although numerous corrective algorithms and methods have been developed to handle this problem (Jares-Erijman and Jovin, 2003), these methods are generally difficult to apply and can introduce additional error into the measurement of FRET. These methods also require extensive controls, which gives rise to additional data-handling and storage issues when adapted to a high-throughput approach. Thus, an optimal solution would require collection of a minimal set of images and corrective processing to determine rigorously the presence or absence of FRET.

SUMMARY OF THE INVENTION

Thus, in accordance with the present invention, there is provided a method of detecting Förster resonance energy transfer comprising (a) applying polarized light to a donor fluorescent molecule in the presence of an acceptor fluorescent molecule that is distinct from the donor fluorescent molecule; and (b) measuring emitted light, wherein a decrease in the amount of anisotropy is directly related to the amount of energy transfer between the acceptor and donor fluorescent molecules. Both polarized and depolarized emitted light may be measured. Polarized emitted light is caused by the fluorescence of the donor fluorescent molecule and fluorescence of the acceptor fluorescent molecule, and wherein polarized fluorescence of the acceptor fluorescence molecule results from direct excitation of the acceptor fluorescence molecule.

The donor fluorescent molecule may exhibit a highly polarized steady-state fluorescence. The donor fluorescent molecule may be a protein or a molecule rigidly attached to a protein or other large molecule (>15,000 m.w.). The protein may be selected from GFP, BFP, CFP, YFP, EGFP, EYFP, Venus, Citrine, phiYFP, copGFP CGFP, ECFP, Cerulean, CyPet, T-Sapphire, Emerald, YPet, AcGFP1, AmCyan, AsRed2, dsRed, dsRed2, dsRed-Express, EBFP, HcRed, ZsGreen, ZsYellow, J-Red, TurboGFP, Kusabira Orange, Midoriishi Cyan, mOrange, DsRed-monomer, mStrawberry, mRFP1, tdTomato, mCherry, mPlum, and mRaspberry.

The BFP protein may be a protein with a peak emission wavelength less than 450 nm, the CFP protein may be a protein with a peak emission wavelength in the range of 450 nm to 480 nm, the GFP protein may be a protein with a peak emission wavelength in the range of 480 nm to 520 nm, the YFP protein may be a protein with a peak emission wavelength in the range of 520 nm to 550 nm, the OFP protein may be a protein with a peak emission wavelength in the range of 550 nm to 575 nm, the RFP protein may be a protein with a peak emission wavelength in the range of 575 nm to 600 nm, the FRFP protein may be a protein with a peak emission wavelength of greater than 600 nm, Where the donor fluorescent protein is BFP, the acceptor fluorescent protein may be CFP. Where the donor fluorescent protein is BFP, the acceptor fluorescent protein may be GFP. Where the donor fluorescent protein is BFP, the acceptor fluorescent protein may be YFP. Where the donor fluorescent protein is BFP, the acceptor fluorescent protein may be OFP. Where the donor fluorescent protein is BFP, the acceptor fluorescent protein may be RFP. Where the donor fluorescent protein is BFP, the acceptor fluorescent protein may be FRFP. Where the donor fluorescent protein is CFP, the acceptor fluorescent protein may be GFP. Where the donor fluorescent protein is CFP, the acceptor fluorescent protein may be YFP. Where the donor fluorescent protein is CFP, the acceptor fluorescent protein may be OFP. Where the donor fluorescent protein is CFP, the acceptor fluorescent protein may be RFP. Where the donor fluorescent protein is CFP, the acceptor fluorescent protein may be FRFP. Where the donor fluorescent protein is GFP, the acceptor fluorescent protein may be YFP. Where the donor fluorescent protein is GFP, the acceptor fluorescent protein may be OFP. Where the donor fluorescent protein is GFP, the acceptor fluorescent protein may be RFP. Where the donor fluorescent protein is GFP, the acceptor fluorescent protein is FRFP. Where the donor fluorescent protein is YFP, the acceptor fluorescent protein may be OFP. Where the donor fluorescent protein is YFP, the acceptor fluorescent protein may be RFP. Where the donor fluorescent protein is YFP, the acceptor fluorescent protein may be FRFP. Where the donor fluorescent protein is OFP, the acceptor fluorescent protein may be RFP. Where the donor fluorescent protein is OFP, the acceptor fluorescent protein may be FRFP. Where the donor fluorescent protein is RFP, the acceptor fluorescent protein may be FRFP. Where the donor fluorescent protein is FRFP, the acceptor fluorescent protein may be a fluorescent protein with a emission peak greater than the donor.

Measuring depolarized light may comprise laser scanning fluorescence microscopy and/or widefield fluorescence microscopy. Polarized light comprises single photon excitation and the wavelength may be less than 425 nm. Polarized light may comprise two-photon excitation and the wavelength is about 800 nm. Measuring may comprise capture of both horizontal and vertical polarizations. The fluorescent donor and/or acceptor molecules may be linked to another molecule.

In another embodiment, there is provided a method of measuring association of two target molecules using Förster resonance energy transfer comprising (a) providing a system comprising a donor fluorescent molecule linked to a first target molecule and an acceptor fluorescent molecule linked to a second target molecule, wherein the acceptor fluorescent molecule is distinct from the donor fluorescent molecule, (b) applying polarized light to the system; and (c) determining depolarization of emitted light, wherein the amount of depolarized light is directly related to the association of the target molecules.

At least one of the target molecules may be a protein, lipid, carbohydrate, or nucleic acid, or both of the target molecules are proteins or nucleic acids. The method may further comprise addition a candidate substance, and the effect of the candidate substance on association of the target molecules may be measured. The method may further comprise assessing the effect of a single candidate substance on multiple target pair associations. The method may further comprise addition of multiple candidate substances and measuring of their effects on a single target pair association.

The donor fluorescent molecule may exhibit a slow rotational diffusion (as would be expected for a molecule >15,000 m.w.). The protein may be selected from GFP, BFP, CFP, YFP, EGFP, EYFP, Venus, Citrine, phiYFP, copGFP CGFP, ECFP, Cerulean, CyPet, T-Sapphire, Emerald, YPet, AcGFP1, AmCyan, AsRed2, dsRed, dsRed2, dsRed-Express, EBFP, HcRed, ZsGreen, ZsYellow, J-Red, TurboGFP, Kusabira Orange, Midoriishi Cyan, mOrange, DsRed-monomer, mStrawberry, mRFP1, tdTomato, mCherry, mPlum, and mRaspberry.

The BFP protein may be a protein with a peak emission wavelength less than 450 nm, the CFP protein may be a protein with a peak emission wavelength in the range of 450 nm to 480 nm, the GFP protein may be a protein with a peak emission wavelength in the range of 480 nm to 520 nm, the YFP protein may be a protein with a peak emission wavelength in the range of 520 nm to 550 nm, the OFP protein may be a protein with a peak emission wavelength in the range of 550 nm to 575 nm, the RFP protein may be a protein with a peak emission wavelength in the range of 575 nm to 600 nm, the FRFP protein may be a protein with a peak emission wavelength of greater than 600 nm, Where the donor fluorescent protein is BFP, the acceptor fluorescent protein may be CFP. Where the donor fluorescent protein is BFP, the acceptor fluorescent protein may be GFP. Where the donor fluorescent protein is BFP, the acceptor fluorescent protein may be YFP. Where the donor fluorescent protein is BFP, the acceptor fluorescent protein may be OFP. Where the donor fluorescent protein is BFP, the acceptor fluorescent protein may be RFP. Where the donor fluorescent protein is BFP, the acceptor fluorescent protein may be FRFP. Where the donor fluorescent protein is CFP, the acceptor fluorescent protein may be GFP. Where the donor fluorescent protein is CFP, the acceptor fluorescent protein may be YFP. Where the donor fluorescent protein is CFP, the acceptor fluorescent protein may be OFP. Where the donor fluorescent protein is CFP, the acceptor fluorescent protein may be RFP. Where the donor fluorescent protein is CFP, the acceptor fluorescent protein may be FRFP. Where the donor fluorescent protein is GFP, the acceptor fluorescent protein may be YFP. Where the donor fluorescent protein is GFP, the acceptor fluorescent protein may be OFP. Where the donor fluorescent protein is GFP, the acceptor fluorescent protein may be RFP. Where the donor fluorescent protein is GFP, the acceptor fluorescent protein may be FRFP. Where the donor fluorescent protein is YFP, the acceptor fluorescent protein may be OFP. Where the donor fluorescent protein is YFP, the acceptor fluorescent protein may be RFP. Where the donor fluorescent protein is YFP, the acceptor fluorescent protein may be FRFP. Where the donor fluorescent protein is OFP, the acceptor fluorescent protein may be RFP. Where the donor fluorescent protein is OFP, the acceptor fluorescent protein may be FRFP. Where the donor fluorescent protein is RFP, the acceptor fluorescent protein may be FRFP. Where the donor fluorescent protein is FRFP, the acceptor fluorescent protein may be a fluorescent protein with a emission peak greater than the donor.

Measuring depolarized light may comprise laser scanning fluorescence microscopy and/or widefield fluorescence microscopy. Polarized light may comprise single photon excitation, wherein the wavelength is less than 425 nm. Polarized light comprises two-photon excitation, wherein the wavelength is about 800 nm. Measuring may comprise capture of both horizontal and vertical polarizations.

In yet another embodiment, there is provided a method of detecting Förster resonance energy transfer comprising (a) applying polarized light to a molecule comprising a donor fluorescent moiety and an acceptor fluorescent moiety molecule, wherein the acceptor fluorescent moiety is distinct from the donor fluorescent moiety; and (b) determining depolarization of emitted light, wherein the amount of depolarized light is directly related to the amount of energy transfer between the acceptor and donor fluorescent moieties.

The molecule may be a protein, a lipid, a carbohydrate or a nucleic acid. The molecule may be subjected to a test condition, and the amount of depolarized light is compared to that observed in the absence of the test condition. The molecule may be a protein and the test condition may be a folding state condition or a protease. The molecule may be a glycoprotein and the test condition may be a folding state condition or a glycosylase. The molecule may be lipid and the test condition may be a lipase. The molecule may be a nucleic acid and the test condition may be a hybridization condition or a nuclease. The molecule may be an autocatalytic protein or nucleic acid.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or." Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A-F—Fluorescence polarization microscopy. (FIG. 3A) Steady-state anisotropy (r) was calculated from fluorescence emission spectra (425 nm excitation) for solutions containing mCerulean (black) and mVenus:mCerulean containing a short linker (red, high FRET efficiency of 0.18) or a long linker (blue, low FRET efficiency of 0.12). Polarization of the donor fluorophore increases in the presence of FRET, while the acceptor fluorescence becomes increasingly depolarized with increased FRET. (FIG. 3B) Excitation scan of mVenus anisotropy (525 nm) (FIG. 3C) Steady-state anisotropy (r) was calculated from fluorescence emission spectra using two-photon excitation (800 nm excitation). (FIG. 3D) Anisotropy images (pseudocolored) of COS7 cells expressing mCerulean, unlinked mVenus and mCerulean, or mVenus:mCerulean with short and long linkers. Anisotropy images were calculated from sensitized emission images taken at parallel and perpendicular polarizations using vertically polarized two photon excitation (800 nm). (FIG. 3E) Widefield images showing expression of unlinked mCerulean and mVenus using cotransfection protocol as in FIG. 3D. (FIG. 3F) Scatter plot of sensitized emission anisotropy data. Each point represents the anisotropy calculated for an individual cell, and mean values are indicated by a line. Calculation of the anisotropy for fluorescence in the acceptor channel reliably distinguishes both the presence and amount of energy transfer.

FIGS. 4A-E—Cartoon representation of the A-FRET principle. (FIG. 4A)

Fluorescence emission from cyan and yellow fluorescence proteins occur in the same plane as the excitation energy (blue arrow). (FIG. 4B) During FRET, excitation energy is transferred to an acceptor of random orientation with respect to the donor excitation plane, resulting in depolarized fluorescence. (FIGS. 4C-E) Beads labeled mCerulean (white circle), mVenus (yellow circle) or linked mVenus:mCerulean (red box) were mixed and examined by fluorescence microscopy. (FIG. 4C) Separation of mCerulean (cyan) and mVenus fluorescence was achieved by spectral imaging and linear unmixing. (FIG. 4D) Vertical (green) and horizontal (blue) polarizations were simultaneously collected in the yellow fluorescence channel. (FIG. 4E) Images from FIG. 4D were processed to generate anisotropy values.

FIGS. 5A-H—Vertical (FIGS. 5A, 5C) and horizontal (FIGS. 5B, 5D) polarizations of cyan (FIGS. 5A, 5B) and yellow (FIGS. 5C, 5D) fluorescence of COS-7 cells co-transfected with mVenus and mCerulean plasmids. Cells were grown on polystyrene 96-well plates prior to scanning with the IsoCyte™ laser scanning fluorimeter. (FIG. 5E) Anisotropy values calculated from images of mCerulean, mVenus, and mVenus:mCerulean beads. (FIG. 5F) mCerulean and mVenus:mCerulean beads were mixed in the same well (black). Plotting the yellow anisotropy versus the cyan anisotropy allows separation of the two populations of beads, as compared with mCerulean (blue) and mVenus:mCerulean (green) beads alone. (FIG. 5G) The anisotropy values of mCerulean, mVenus, mVenus:mCerulean, or coexpression of unlinked mCerulean and mVenus was determined in transfected COS-7 cells. (FIG. 5H) Use of mCerulean anisotropy as an internal reference standard in A-FRET determination.

FIGS. 6A-D—COS-7 cells expressing SCAT3.1 were treated with staurosporine, and imaged using A-FRET microscopy. Images shown are (FIG. 6A) immediately after treatment and (FIG. 6B) after 5 hours. Cleavage of the SCAT sensor results in a disproportional decrease in the horizontal yellow emission (blue) compared with vertically polarized emission (green). (FIG. 6C) Intensity vs. time traces of vertical (blue dashed line) and horizontal (black line) yellow fluorescence for cells 1-5 as shown in (FIG. 6A). (FIG. 6D) Histogram of anisotropy values from untreated (white, n=705) and apoptotic (black, n=184) COST cells grown expressing SCAT3.1 and scanned using the IsoCyte™. Cells were treated with a high dose (10 μM) of $H_2O_2$ for 90 min to induce apoptosis.

DESCRIPTION OF ILLUSTRATIVE EMBODIMENTS

I. The Present Invention

Figure 1:
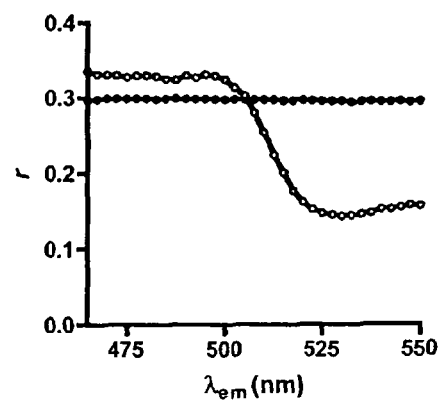
FIG. 1—Steady-state anisotropy (r) was calculated from fluorescence emission spectra (425 nm excitation) for solutions containing thre FRET donor, mCerulean (●) and a fusion protein containing the FRET acceptor, mVenus, linked to mCerulean (○). FRET between mCerulean and mVenus results in increased mCerulean (475 nm) anisotropy from a decreased fluorescence lifetime, and depolarized sensitized emission from mVenus (525 nm). Analysis of recombinantly generated proteins was performed as previously described (Rizo et al., 2004).

As discussed above, fluorescent proteins, first derived from *Aequorea victoria* and more recently from many other species are powerful tools in examining the biological relationship of various molecules in situ. In particular, it is common to fuse proteins of interest to fluorescent proteins in order to track protein localization and function in living cells. Modification of the DNA sequence of the original *Aequorea victoria* green fluorescent protein (GFP) has produced several variants of fluorescent proteins with unique spectral and biochemical properties suitable for a wide variety of applications, including the cyan fluorescent protein (CFP) and yellow fluorescent protein (YFP). These two molecules exhibit special overlapping fluorescence excitation and emission properties that are suited to measurement of close molecular distances, in particular, by Förster, or fluorescence, resonance energy transfer (FRET).

However, as discussed above, there are significant difficulties associated with FRET measurements, such as (a) the relatively small changes in energy transfer are difficult to measure between FRET partners with broadly overlapping spectra, such as fluorescent proteins; (b) crosstalk emission of the CFPs can register in the YFP detection channel, which leads to a "false positive" indication of FRET; and (c) crosstalk excitation of the donor YFPs also leads to a "false positive" indication of FRET. Although corrective algorithms and methods have been developed to handle this problem (Jares-Erijman and Jovin, 2003), these methods are generally difficult to implement, time consuming to perform, requiring of extensive control experiments, and/or susceptible to creating additional error in the measurements.

Therefore, the inventors decided to take advantage of the fact that fluorescence emission from fluorescent proteins is highly polarized, while sensitized emission from an acceptor fluorescent protein is depolarized. Experimentally, this approach has been shown to offer a dynamic range of 15 to over 150, as opposed to fluorescence lifetime imaging (the most rigorous FRET measurement method so far developed) that gives a dynamic range of less than 10. Thus, this approach offers a tremendous advantage over currently employed systems for measuring FRET. The new method is also fast and simple, requiring just two images to be acquired, and only image arithmetic for data reduction.

II. Fluorescent Proteins

*Aequorea victoria* are brightly luminescent jellyfish, with glowing points around the margin of the umbrella. Light arises from yellow tissue masses that each consist of about 6000-7000 photogenic cells. The cytoplasm of these cells is densely packed with fine granules that contain a Ca++ activated photoprotein, aequorin, that emits blue-green light, and an accessory green fluorescent protein (GFP), which accepts energy from aequorin and re-emits it as green light. GFP is an extremely stable protein of 238 amino acids, stable in neutral buffers up to 65° C., and displaying a broad range of pH stability from 5.5 to 12. The protein is intensely fluorescent, with a quantum efficiency of approximately 80% and molar extinction coefficient of $2.2 \times 10^4$ cm$^{-1}$ M-1 (after correction for the known molecular weight). GFP fluoresces maximally when excited at 400 nm with a lesser peak at 475 nm, and fluorescence emission peaks at 509 nm. Since the purification and cloning of the GFP from *Aequorea Victoria*, similar fluorescent proteins have been isolated and cloned from many other species including dynoflagelates, sea pens, and reef corals.

Two variants of the *Aequorea victoria* GFP, cyan fluorescent protein (CFP) and yellow fluorescent protein (YFP), have special fluorescence excitation and emission properties that are well suited to measurement of close molecular distances. Thus, variants of this type have been the most widely used for FRET experiments. When these two molecules are positioned at distances closer than 7 nm of each other, energy transfer can occur from the excited state of the donor molecule (CFP), to the unoccupied excited state of the acceptor molecule (YFP) by a process commonly referred to as fluorescence (or Förster) resonance energy transfer (FRET). FRET between CFP and YFP can be detected using a wide variety of spectroscopic and fluorescence microscopy techniques and is often used to report protein-protein interactions or changes in the conformation state of a peptide or protein. Since the efficiency of FRET is directly related to the spectroscopic properties of both the donor and acceptor molecules, improvements can be made to the fluorescence properties of the fluorophores, such as to increase both the FRET efficiency and the chances of successful detection. FRET has also been used to quantify association of a protein of interest with an organelle (Chiu et al., 2002). As more fluorescent proteins are developed, other FRET pairs are being tried, such as the CFP to an Orange FP from reef coral, called mKO (Karasawa et al., 2004). One of the strengths of the present invention is that it is broadly applicable to any pair of fluorescent proteins that have spectral properties sufficient to generate FRET.

The gene of the green fluorescent protein has been isolated and its sequence has also been determined (Prasher et al., 1992). There have also been numerous reports of amino acid sequences of other fluorescent proteins or their mutants, for example, as described in Tsein (1998) and the literature cited therein. Fluorescent proteins include green fluorescent protein, red fluorescent protein, yellow fluorescent protein, GFP, BFP, CFP, YFP, EGFP, EYFP, Venus, Citrine, phiYFP, copGFP CGFP, ECFP, Cerulean, CyPet, T-Sapphire, Emerald, YPet, AcGFP1, AmCyan, AsRed2, dsRed, dsRed2, dsRed-Express, EBFP, HcRed, ZsGreen, ZsYellow, J-Red, TurboGFP, Kusabira Orange, Midoriishi Cyan, mOrange, DsRed-monomer, mStrawberry, mRFP1, tdTomato, mCherry, mPlum, and mRaspberry.

The term "cyan fluorescent protein (CFP)" as used herein is defined as any fluorescent protein with an absorption maximum between 420 and 460 nm, and a fluorescence maximum between 460 and 500 nm. These proteins have mainly been derived from the wild-type *Aequoria* GFP with a Y66W mutation, resulting in a primary excitation peak at ~434 nm with minor excitation maxima at ~452 nm, and a primary emission peak is 477 nm with minor shoulder at ~505 nm (Heim et al., 1994). Other fluorescent proteins are termed "green fluorescent protein (GFP)", meaning proteins with absoption maxima between 480 and 500 nm and fluorescence maxima between 500 and 515 nm, and "yellow fluorescent protein (YFP)" meaning proteins with absoption maxima between 500 and 520 nm and fluorescence maxima between 515 and 535 nm.

III. Förster Resonance Energy Transfer (FRET) and Polarization/Depolarization FRET is a phenomenon in which the excited-state enrgy in one molecule (called the donor) is transferred to another molecule by a radiationless coupling. This mechanism was first correctly described by Förster, and differs from other types of energy transfer, such as electron sharing (Dexter) or trivial transfer (emission of a photon from the donor and reabsorption by the acceptor). The Dexter mechanism requires the two molecules to be in physical contact, while trivial transfer is a very low probability. In contrast, the Förster mechanism exhibits a high probability when the two molecules are within the Förster radius, which is defined for any given pair of fluorophores.

The overall FRET efficiency depends on the Förster radius, and is determined by several factors and is directly related to the amount of overlap between the absorption spectra of the acceptor molecule and the emission spectra of the donor molecule. The amount of FRET also depends on the alignment of the donor and acceptor molecules, although most biological systems are not ridgidly aligned. The FRET efficiency is also affected by the ability of the acceptor molecule to absorb light, as indicated by its molar extinction coefficient, and the overall stability of the excited state of the donor molecule, as indicated by the probability that absorption will lead to fluorescence (quantum yield) and the lifetime of the excited state.

FRET between two different fluorophores can be assayed by several methods: looking at the change in color of the fluorescence, measuring the fluorescence lifetime of the donor, examining the changes upon photobleaching either the donor or acceptor, or as we show in this new invention: by measuring the fluorescence polarization of the acceptor. Regardless of the approach, most of these assays share common features of the instrumentation.

The types of the microscope used to measure FRET can be suitably selected depending on the purpose. If frequent observations are necessary for monitoring a time course of the changing, conventional incident-light fluorescent microscope is preferred. If resolution is to be increased as in the case where detailed intercellular localization is to be monitored, confocal laser microscope is preferred. As a microscope system, an inverted microscope is preferred for most live cell measurements in view of keeping the physiological state of cell and preventing contamination. When an upright microscope is used, a water immersion lens can be used in the case of using lens of high power.

The filter set can be suitably selected depending on the fluorescent wave length of the fluorescent protein. For the observation of GFP, it is preferred to use a filter with excitation light of about 470-490 nm and fluorescent light of about 500-520 nm. For the observation of YFP, it is preferred to use a filter with excitation light of about 490-510 nm and fluorescent light of about 520-550 nm. For the observation of CFP, it is preferred to use a filter with excitation light of about 425 nm and fluorescent light of about 460-500 nm. For the purposes of the present invention, there are no specific requirements in terms of microscopes and filters, except that it would be useful to minimize the use of depolarizing elements in the light path. Microscope manufacturers all market strain-free optics for polarized light measurements in transmission and reflection microscopy, and such optics would be helpful for these polarized fluorescence measurements as well.

Moreover, when time course observation is carried out in living cells by using a fluorescent microscope, the cells should be photographed in a short period, and therefore a high sensitive cooled CCD camera is used. By using a cooled CCD camera, thermal noise can be decreased by cooling CCD, and weak fluorescent image can be clearly acquired by exposure of short period. Confocal microscopes can also be used for live cell imaging, as long as care is taken to minimize the exposure times.

The issues that are particular to this invention involve the polarization of the donor excitation and the acceptor emission. The steady-state polarization of a fluorophore is directly related to its rotational diffusion and the length of its fluorescence lifetime. The shorter the lifetime and slower the rotation, the more highly polarized the fluorescence. The amount of polarization of the fluorescence is expressed as the anisotropy of the fluorophore. The maximum value is 0.4 for single photon excitation, and GFPs in solutions such as the cell cytoplasm have a steady-state anisotropy value of about 0.3. A highly depolarized fluorescence signal will have an anisotropy value less than 0.1. For two-photon excitation, fluorescence excitation is even more highly polarized, and the theoretical maximum is 4/7 (or approximately 0.57). Generally, anisotropy values above 0.3 are considered highly polarized, and values less than 0.2 are considered depolarized.

What is measured in the current invention is a combination of fluorescence arising from FRET and the crosstalk excitation of the acceptor, so the presence of FRET would be indicated absolutely by a general decrease in the anisotropy as a function of the increasing proportion of FRETing molecules. With GFPs, this works well since the anisotropy starts at a rather high 0.3 and decreases from there. The absolute value of the steady-state anisotropy is ultimately less important than the fact that it decreases in the presence of FRET.

One of the strengths of the current invention is that almost any existing fluorescence microscope of high-throughput screening system can be easily modified to use polarization as a high-contrast FRET assay. All that is required is a polarizer in the excitation path and another in the emission collection optics. In practice, both of these should be rotatable to allow the collection of all four combinations of excitation and emission polarizations as described in the example below (vertical excitation-vertical emission; vertical excitation-horizontal emission; horizontal excitation-vertical emission; horizontal excitation-horizontal emission). The polarization behavior of light in a microscope is well understood through many years of the use of polarized light in transmission and reflection microscopy to examine material structure, and through the use of polarization in optical contrast methods such as Nomarski DIC. Polarization of fluorescence has not yet been used extensively in microscopy as a contrast mechanism. It is known, however, how to correct from the effects of focusing polarized light through the objective lens of the microscope (Axelrod, 1989). These corrections have been used to assay homo-energy transfer in fluorescence microscopy (Blackman et al., 1996; Rocheleau et al., 2003), and can be easily applied to the current invention.

IV. Methods Used to Prepare FRET Experiments

1. Fusion Proteins

A fused fluorescent protein can be constructed by fusing a fluorescent protein of the present invention with another protein. The kinds of "another protein" to be fused with the fluorescent protein for use in the present invention are not particularly limited. The methods for obtaining the fused fluorescent protein of the present invention are not limited. There may be used any of a chemically synthesized protein fusion, or a recombinant protein produced by a gene recombination technique.

In the case of producing a recombinant protein, it is necessary to obtain the DNA encoding the protein. Further, a DNA fragment encoding a protein to be fused may also obtained. Then, DNA encoding the desired fused fluorescent protein can be obtained by ligating those DNA fragments in order by means of a gene recombination technique. A fused fluorescent protein of the present invention can be produced by introducing this DNA into a suitable expression system.

By expressing the fused fluorescent protein obtained by fusing the fluorescent protein of the present invention with another protein (referred to as "protein X") as mentioned above in cells and monitoring the emitted fluorescence, the localization and dynamic situation of protein X in the cell can be analyzed. Thus, by observing a cell which was transformed or transfected with DNA encoding the fused fluorescent protein of the present invention by means of a fluorescent microscope, the localization and dynamic situation of protein X in the cell can be visualized and analyzed.

For example, by using a protein which is specific for intercellular organelles as protein X, distribution and movement of nucleus, mitochondrion, endoplasmic reticulum, secretory vesicles, peroxisome and the like can be observed. Moreover, since axon and dendroid axon of nerve cells show very complicated change of running direction in developing individuals, dynamic analysis can be carried out by labeling such sites with a fluorescence. Various targeting sequences are commercially available, such as DsRed2 subcellular localization vectors from Clontech, which facilitate nuclear, mitochondrial, peroxisomal and ER targeting.

2. Protein Purification

It may be desirable to purify fluorescent or fusion proteins in accordance with the present invention. Protein purification techniques are well known to those of skill in the art. These techniques involve, at one level, the crude fractionation of the cellular milieu to polypeptide and non-polypeptide fractions. Such methods may include physical disruption followed by centrifugation, solvent extraction, salting-out (e.g., by ammonium sulfate or the like), desalting, precipitation, etc. Having thus separated generally the polypeptide from other molecules, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

The term "purified protein" as used herein is intended to refer to a proteinaceous composition, isolated from other components, wherein the protein or peptide is purified to any degree relative to its naturally-obtainable state. A purified protein or peptide therefore also refers to a protein or peptide, free from the environment in which it may naturally occur. Generally, "purified" will refer to a protein composition that has been subjected to fractionation to remove various other components, and which composition substantially retains its expressed biological activity. Where the term "substantially purified" is used, this designation will refer to a composition in which the protein forms the major component of the composition, such as constituting about 50%, about 60%, about 70%, about 80%, about 90%, about 95% or more of the proteins in the composition.

Various methods for quantifying the degree of purification of the protein will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein.

There is no general requirement that the protein always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

V. Nucleic Acids and Expression Constructs

Certain embodiments of the present invention concern a nucleic acid encoding optimized cyan fluorescent proteins. In particular aspects, the nucleic acid is a cDNA. The term "nucleic acid" is well known in the art, and generally refers to a molecule (i.e., a strand) of DNA, RNA or a derivative or analog thereof. The term "nucleic acid" encompasses the terms "oligonucleotide" and "polynucleotide," each as a subgenus of the term "nucleic acid." The term "oligonucleotide" refers to a molecule of between about 3 to about 50 nucleobases in length. The term "polynucleotide" refers to at least one molecule of greater than about 50 nucleotides in length.

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 0 266 032, incorporated herein by reference, or via deoxynucleoside H-phosphonate intermediates as described by Froehler et al. (1986) and U.S. Pat. No. 5,705,629, each incorporated herein by reference. In the methods of the present invention, one or more oligonucleotide may be used. Various different mechanisms of oligonucleotide synthesis have been disclosed in for example, U.S.

Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al., 2001, incorporated herein by reference).

In certain aspect, the present invention concerns a nucleic acid that is an isolated nucleic acid. As used herein, the term "isolated nucleic acid" refers to a nucleic acid molecule (e.g., an RNA or DNA molecule) that has been partially or substantially isolated free of total genomic and in vitro reaction products. In certain embodiments, "isolated nucleic acid" also refers to a nucleic acid that has been isolated free the bulk of cellular components or in vitro reaction components. A nucleic acid may be purified on polyacrylamide gels, cesium chloride centrifugation gradients, or by any other means known to one of ordinary skill in the art (see for example, Sambrook et al., 2001, incorporated herein by reference).

1. Vectors

As discussed above, the term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1990 and Ausubel et al., 1996, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra. A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression (see, for example Sambrook et al. 2001, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, vvww.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Table 1 lists non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

PROMOTER AND/OR ENHANCER

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| α₁-Antitrypsin | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne | Klamut et al., 1990 |

TABLE 1-continued

PROMOTER AND/OR ENHANCER

| Promoter/Enhancer | References |
|---|---|
| Muscular Dystrophy | |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

INDUCIBLE ELEMENTS

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al.,1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor α | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki et al., 1998), D1A dopamine receptor gene (Lee et al., 1997), insulin-like growth factor II (Wu et al., 1997), and human platelet endothelial cell adhesion molecule-1 (Almendro et al., 1996).

Examples of promoters which are operative in bacterial cells include, a promoter of *Bacillus stearothermophilus* maltogenic amylase gene, *Bacillus licheniformis* α-amylase gene, *Bacillus amyloliquefaciens* BAN amylase gene, *Bacillus subtilis* alkaline protease gene, or *Bacillus pumilus* xyloslidase gene; a $P_R$ or $P_L$ promoter of phage lambda; a lac, trp, or tac promoter of *Escherichia coli*; and the like.

Examples of promoters which are operative in insect cells include polyhedrin promoter, P10 promoter, basic protein promoter of *Autographa californica* nuclear polyhedrosis, baculovirus immediate early gene 1 promoter, baculovirus 39K delayed early gene promoter, and the like. Examples of promoters which are operative in yeast host cells include a promoter derived from yeast glycolysis system genes, alcohol dehydrogenase gene promoter, TPI1 promoter, ADH2-4-c promoter, and the like.

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392. Further useful plasmid vectors include pIN vectors (Inouye et al., 1985), and pGEX vectors, for use in generating glutathione S-transferase (GST) soluble fusion proteins for later purification and separation or cleavage. Other suitable fusion proteins are those with β-galactosidase, ubiquitin, and the like.

Another vector of interest is the "PEST" vector, pd4EGFP-Bid, from Clontech. This is a mammalian expression vector that encodes a fusion of destabilized enhanced green fluorescent protein (d4EGFP) and Bid, a member of the Bcl-2 "pro-apoptosis" family. Because of its fluorescent label, the Bid-d4EGFP fusion is easily detected by microscopy, allowing researchers to track its movements in response to certain apoptotic stimuli. To drive expression of the fluorescent fusion, pd4EGFP-Bid contains the immediate early promoter of cytomegalovirus, positioned just upstream of the Bid sequence. A short linker joins the Bid coding sequence to the 5'-end of d4EGFP. Farther downstream, the vector contains a pair of SV40 polyadenylation signals, which direct proper processing of the 3' end of the Bid-d4EGFP mRNA. The vector also contains an SV40 origin for replication in mammalian cells expressing the SV40 T antigen, a pUC origin of replication for propagation in *E. coli*, and an f1 origin for single-stranded DNA production. A neomycin-resistance cassette (Neo), consisting of the SV40 early promoter, the neomycin/kanamycin resistance gene of Tn5, and polyadenylation signals from the HSV TK gene, allows stably transfected eukaryotic cells to be selected using G418. A bacterial promoter upstream of the cassette confers kanamycin resistance ($Kan^r$) to *E. coli*. d4EGFP, a destabilized, red-shifted excitation variant of *Aequorea victoria* GFP, serves not only as a label, but also as a device to ensure protein turnover.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

2. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985).

b. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

c. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

d. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

e. Sonication Loading

Additional embodiments of the present invention include the introduction of a nucleic acid by direct sonic loading. LTK⁻ fibroblasts have been transfected with the thymidine kinase gene by sonication loading (Fechheimer et al., 1987).

f. Liposome-Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution.

Current formulations use a DNA condensing agent, such as protamine suflate, along with "helper lipids" (Reddy et al., 2002) describe a folate-targeted, cationic lipid based transfection complex was developed and found to specifically transfect folate receptor-expressing cells and tumors. These liposomal vectors were comprised of protamine-condensed plasmid DNA, a mixture of cationic and neutral lipids, and a folic acid-cysteine-polyethyleneglycol-phosphatidylethanolamine (FA-Cys-PEG-PE) conjugate. Overall, folate-labeled formulations produced an 8- to 10-fold increase in expression, as compared with the corresponding non-targeted cationic lipid/DNA formulations.

Hong et al. (1997) describe stable complexes of cationic liposomes with plasmid

DNA were prepared by (1) including a small amount of polyethyleneglycol-phospholipid conjugate or (2) condensing the DNA with polyamines prior to the formation of liposome-plasmid complexes. These preparations were stable for months at 4° C. and gave reproducible high transfection activity for in vivo gene delivery. In these formulations cholesterol, not dioleoylphosphatidylethanolamine, was the helper lipid effective for sustaining high transfection activity in vivo.

Commercially available lipofection reagents include Cell-Phect Transfection Kit (Amersham-Pharmacia Biotech), CytoFectene Reagent (Bio-Rad), CLONrectin Reagent (Clontech), Cytofectin (Glen Research), Perfect Lipid™ Transfection Kit (Invitrogen), EuFectin (JBL Scientific), Lipofectamine™ 2000, Lipofectamine Plus™, Lipofectamine™, DMRIE-C Reagent (Life Technologies), ExGen 500 (MBI Fermentas), TransT LT-1 and LT-2 (PanVera), Transfast™ and Tr$_x$™ Reagents (Promega), SuperFect™ Transfection Reagent (Qiagen), LipoTAXI™ (Stratagene) and Genetransfer HMG-1,-2 Mixture (Wako Chemicals USA).

g. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

h. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

3. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art (see, for example, webpage phylogeny.arizona.edu/tree/phylogeny.html). A host cell into which the DNA or recombinant vector of the present invention is introduced may be a bacteria, yeast, fungi, or higher eukaryotic cell.

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as Gram-negatives like *E. coli* (e.g., *E. coli* strain RR1, *E. coli* LE392, *E. coli* B, *E. coli* X 1776 (ATCC No. 31537) as well as *E. coli* W3110 (F—, lambda-, prototrophic, ATCC No. 273325), DH5α, JM109, and KC8, Gram-positive bacteria such as *Streptomyces, Bacillus* species (e.g., *subtilis*); and other enterobacteriaceae such as *Salmonella typhimurium, Serratia marcescens*, various *Pseudomonas* specie, as well as a number of commercially available bacterial hosts such as SURE® Competent Cells and SOLOPACK™ Gold Cells (STRAT-AGENE®, La Jolla).

Other examples of fungal cells are filamentous bacteria, for example *Aspergillus, Neurospora*, and *Fusarium*, and cells belonging to *Trichoderma*. When a filamentous bacterium is used as a host cell, transformation can be performed by integrating the DNA construct into the host chromosome and obtaining a recombinant host cell. Integration of the DNA construct into the host chromosome can be performed according to a known method such as homologous recombination or heterologous recombination.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Examples of yeast cells include cells belonging to *Saccharomyces* or *Schizosaccharomyces*, and examples include *Saccharomyces cerevisae* and *Saccharomyces kluyveri*.

When an insect cell is used as a host, a protein can be expressed by co-transfecting a recombinant gene transduction vector and a baculovirus into the insect cell to obtain a recombinant virus in the insect cell culture supernatant, and then infecting the recombinant virus into the insect cell (for example, as described in Baculovirus Expression Vectors, 1988, and the like).

As a baculovirus, for example, *Autographa californica* nuclear polyhedrosis virus, which is a virus that infects *Mamestra*-family insects, and the like, can be used. As an insect cell, for example, Sf9 and Sf21, which are ovarian cells of *Spodoptera frugiperda*, and Hi Five, which is an ovarian cell of *Trichoplusia ni* (Invitrogen), or the like can be used.

4. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. No. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide.

It is contemplated that the proteins produced by the methods of the invention may be "overexpressed," i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide in comparison to the level in natural cells is indicative of overexpression, as is a relative abundance of the specific protein in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g., 8M) or chaotropic agents such as guanidine hydrochloride in the presence of reducing agents, such as β-mercaptoethanol or DTT (dithiothreitol), and refolded into a more desirable conformation, as would be known to one of ordinary skill in the art.

VI. Screening Formats

The present invention facilitates various screening assays that utilize fluorescent proteins. Of particular interest are assays that track protein position within a cell, tissue, organ or organism, including those that monitor the association or dissociation of two distinct fluorescent labels. Such assays may comprise random screening of large libraries of candidate substances for a related activity; alternatively, the assays may be used to focus on particular classes of compounds selected with an eye towards structural attributes that are believed to make them more likely to modulate the function of interest.

To identify a modulator, one generally will determine the function of interest in the presence and absence of the candidate substance, a modulator defined as any substance that alters function. For example, a method generally comprises:
(a) providing a candidate modulator;
(b) providing the candidate modulator to a cell that contains a pair of fluorescent molecules capable of FRET;
(c) subjecting the cell to polarized light;
(d) measuring emission of depolarized light from the cell; and
(e) assessing the amount of FRET based on depolarized emission.

As stated above, assays may be conducted in cell free systems, in isolated cells, tissues or organs, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

1. Modulators

As used herein, the term "candidate substance" refers to any molecule that may potentially inhibit or enhance an activity or characteristic of interest. In one example, the substance will promote or inhibit assocation of two proteins. In another embodiment, the compounds will be capable of cleaving a molecule between two labels. The candidate substance may be a protein or fragment thereof, a small molecule, or even a nucleic acid molecule.

Using lead compounds to help develop improved compounds is know as "rational drug design" and includes not only comparisons with know inhibitors and activators, but predictions relating to the structure of target molecules. The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators. Other suitable modulators include antisense molecules, ribozymes, and antibodies (including single chain antibodies), each of which would be specific for the target molecule.

2. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of an in vitro assay is a binding assay. While not directly addressing function, the ability of a modulator to bind to a target molecule or modulate the binding of two target molecules is strong evidence of a related biological effect. For example, binding of a molecule to a target, or the inhibition of binding of two targets by a molecule, may in and of itself be inhibitory due to steric, allosteric or charge-charge interactions. The target(s) may be either free in solution, fixed to a support, expressed in or on the surface of a cell. The targets are usually labeled, but the candidate substance may also be labeled. A target may also be doubly labeled, and the candidate substance may effect cleavage, and hence lowers FRET.

3. In Cyto and In Vivo Assays

The present invention also contemplates the screening of compounds for their ability to modulate various functions in cells, including intracellular localization and trafficking and proteolytic cleavage. Depending on the assay, culture may be required. In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In one such assay, candidate substance labeled with a fluorescent protein is administered to an animal and its distribution is assesed. Alternatively, the distribution of labeled target molecule is assessed in the presence and absence of a candidate substance. Assessing may include obtaining a small sample (e.g., blood, urine, tissue) from an animal, or it may involve sacrificing the animal to obtain whole organ or even whole organism information.

VI. Microscopy

In order to measure polarized versus depolarized fluorescent emissions, including in high-throughput formats, one can modify commercially available systems. The basic approach is to use a polarized excitation light (lamp or unpolarized laser beam+vertically polarizing filter, or a polarized laser beam), and emission polarizing filters or beamsplitters that restrict fluorescence collection to vertically and horizontal polarizations. In a fluorescence microscope, it is possible to insert the excitation polarizer between the lamp and the excitation filter. Typically, there are not rotatable polarizers available for the excitation path, but this is due to lack of demand rather than any technical limitation. Confocal microscopes generally use lasers that are inherently polarized, so no polarizer is required in the excitation path. In this case a polarization rotating element (such as a half-wave plate would be required to obtain all four polarization combinations. On the emission pathway, there is generally a polarization slider that would usually not be used for fluorescence, but would be inserted if Nomarski DIC is used. Fluorescence microscope manufacturers offer a rotatable polarizer for this position in many available systems. This polarizer requirement is the same whether a conventional fluorescence microscope or a confocal microscope is used.

For high-throughput screening applications, it would be necessary to insert rotatable polarizers on both the excitation and emission optical paths. While there is no technical limitations to this, each manufacturer would need to engineer this for their system.

VII. Examples

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

To devise a simple method for detecting CFP:YFP FRET and to eliminate the observance of false positive results stemming from crosstalk excitation of YFP, the inventors have taken advantage of the large size and slow rotational diffusion of fluorescent proteins. Fluorescence emission from fluorescent proteins is highly polarized, as indicated by steady-state anisotropy values of approximately 0.296 for the monomeric variant of Cerulean (mCerulean) (Rizzo et al., 2004; Zacharias et al., 2002) (FIG. 1). Sensitized emission from an acceptor fluorescent protein (mVenus) conjoined to mCerulean is depolarized (r=0.145 at 525 nm). Since anisotropy is typically measured to an accuracy of greater than 0.001 in cuvettes, and 0.01 in a microscope, this approach offers a dynamic range of 15 to over 150. In comparison, fluorescence lifetime imaging of the same FRET pair shows changes of ~0.6 nsec with a resolution of 0.1 nsec for a dynamic range of less than 10.

Sensitized emission is highly depolarized because the orientation of emitted light is not wholly constrained by the excitation polarization. Thus, sensitive and high-contrast isolation of sensitized emission is achieved. This approach has the particular advantage of eliminating false positives, since systematic artifacts, such as crosstalk excitation of the FRET acceptor, results in increased polarization. This is consistent with our observation that the greatest contrast in polarization occurs at wavelengths that have been optimized for exclusive donor excitation. For single photon excitation, wavelengths less than 425 nm work best, while 800 nm is optimal for two-photon excitation of the Cerulean:Venus FRET pair.

The inventors were able to adapt fluorescence polarization microscopy (Blackman et al., 1996) for measurement of FRET using either a widefield or laser scanning approach. Vertically polarized excitation of the donor was used in combination with capture of both horizontal (VH) and vertical polarizations (VV). Anisotropy (r) images were then calculated using the equation:

$$r = \frac{VV - gVH}{VV + 2gVH}$$

where the g corrects for polarization bias in the instrument (the g-factors that were used for widefield and laser scanning image processing were 1 and 0.75 respectively; Blackman et al., 1996).

Figure 2:
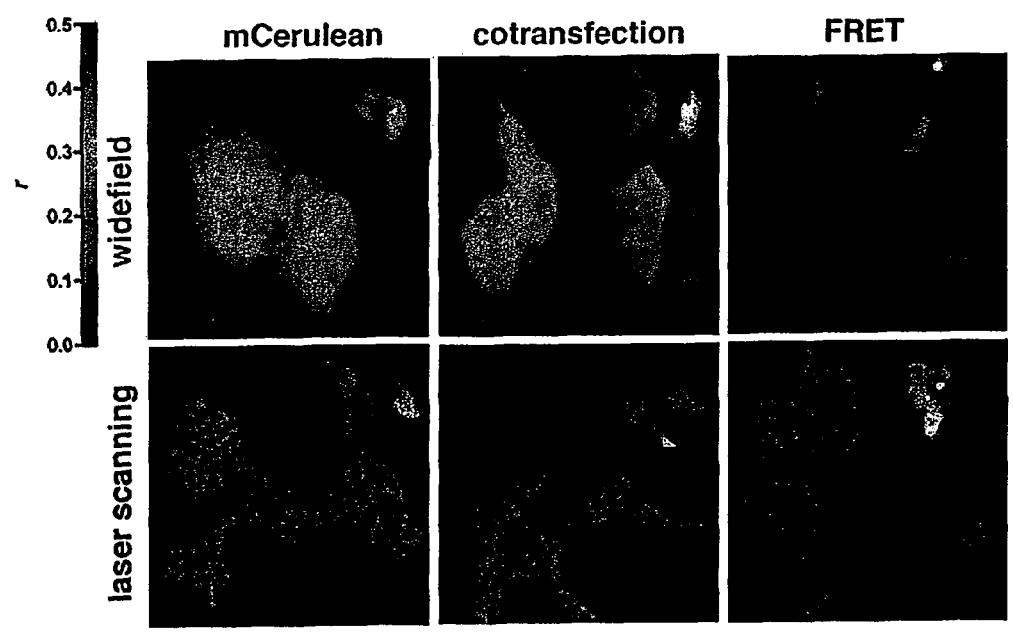
FIG. 2—COS7 cells expressing mCerulean, unlinked mVenus and mCerulean, or a linked mVenus:mCerulean fusion protein (FRET) were imaged using polarized widefield excitation or two-photon laser scanning microscopy. Anisotropy images (pseudocolored) were calculated from sensitized emission images taken at parallel (inset) and perpendicular polarizations.

Widefield and laser scanning fluorescence polarization microscopy was used to image COST cells expressing mCerulean, contransfected mCerulean and mVenus, or a linked mVenus:mCerulean FRET pairing (FIG. 2). The polarization of sensitized emission was examined (520 nm-550 nm for widefield; 515-540 nm for laser scanning) under conditions of vertically polarized donor excitation (425 nm-445 nm for widefield; 800 nm for laser scanning two-photon excitation). Bleed though emission of the donor mCerulean fluorescence is highly polarized, and thus gives a high anisotropy value using both approaches. Anisotropy values from two-photon excitation is slightly higher and results from more highly polarized excitation that is inherent to two-photon absorption. Cotransfection of mCerulean with the mVenus acceptor did not affect fluorescence polarization. Even under conditions of direct excitation of the mVenus, the fluorescence would remain highly polarized. A reduction in fluorescence anisotropy was observed only in the presence of FRET from linked mVenus and mCerulean.

Measurement of changes in fluorescence anisotropy has been previously used to quantify changes in homotransfer, but its application to the measurement of heterotransfer has been limited to a corrective approach (Jares-Erijman and Jovin, 2003; Mattheyses et al., 2004). Thus, measurement of polarized sensitized emission has been overlooked as a simple and high contrast method for determining the presence of FRET. This approach works best when donor fluorescence is highly polarized, as is the case for FRET between fluorescent proteins. In addition, this method of FRET detection is particularly resistant to errors that produce false positives in other assays, including changes in acceptor concentration and inner filtration effects. Therefore, this method is particularly well suited for adaptation for high-throughput screening.

Example 2

A. Methods

Sample Preparation. Beads from a 5 ml HiTRAP chelating HP column (Amersham Biosciences) were charged using a 0.1M NiSO (Rizzo and Piston, 2005) solution and washed with 50 mM TrisHCl. The beads were then labeled as described (Youvan et al., 1997) with purified mCerulean, mVenus, or a linker protein containing mVenus and mCerulean separated by the linker sequence SGLRSPPVAT. Histadine-tagged recombinant protein was bacterially expressed and purified as previously described (Rizzo et al., 2004). For living cell studies, plasmid DNA encoding FP constructs were introduced was into COS-7 cells using FUGENE (Roche) transfection reagent according to the manufacturer's instructions. Cells were seeded onto No. 1 coverglass bottomed dishes (Mat-Tek) for microscopy studies, and polysterene bottom 96-well dishes (BD Falcon).

Fluorescence Imaging. Spectral imaging and linear unmixing were performed as previously described on an LSM510 system (Carl Zeiss Microlmaging, Inc., Thornwood, N.Y.) coupled to a MIRA 900 TiSa laser (Coherent Inc., Santa Clara, Calif.). For anisotropy imaging, a half-wave plate was used to adjust excitation polarization (800 nm). Fluorescence emission was filtered through a 515-540 nm bandpass filter and 2 mm BGG22 glass prior to separation vertical and horizontal polarizations with a broadband polarizing cube beam splitter (Newport). Thin film polarizers (Chroma) were used to further isolate each polarization prior to collection with photomultiplier tubes in a non-descanned configuration.

An IsoCyte™ laser scanning fluorimeter (Blueshift Biotechnologies Inc.) equipped with a 440 nm solid-state laser (Omicron) as the excitation source was used to scan cells and beads seeded in glass bottom 384-well (MatriCal) or polysterene bottom 96-well plates (BD Falcon). For anisotropy measurements, two polarizing filters (Edmond Scientific) were placed in the dualoptical collection head aligned either parallel or perpendicular to the excitation laser polarization. The two independent polarization channels were then each split by a 500 nm longpass beamsplitter into two, creating four channels total. Emissions were color selected with either a 480 nm-510 nm bandpass filter for cyan fluorescence, or a 520 nm longpass filter for yellow fluorescence (Omega Optical).

Image processing and calculation of anisotropies were as previously described (Rizzo and Piston, 2005; Axelrod, 1979).

B. Results

To test the suitability of A-FRET for separation of FRET from non-FRET conditions, metal chelating agarose beads5 were labeled with monomeric Cerulean FP (Zacharias et al., 2002; Rizzo et al., 2004), monomeric Venus FP (Zacharias et al., 2002; Nagai et al., 2002), or a fused Cerulean:Venus FRET pair. The beads were then mixed and imaged using confocal fluorescence microscopy. Spectral imaging and unmixing of Cerulean and Venus fluorescence allows clean separation of beads containing Cerulean alone (FIG. 4C, white circle), from Venus beads (FIG. 4C, yellow circle), and FRET beads (FIG. 4C, red box). However, separation of Venus beads from FRET beads was much less distinct, due to the disparity of brightness between yellow FPs and cyan FPs. Consequently, for low quantities of FRET pairs, cyan fluorescence fades into the noise, making these beads less distinguishable from Venus beads. In contrast, vertical and horizontal polarizations can be imaged simultaneously for the yellow fluorescence channel in the presence of vertically polarized excitation. Cerulean and Venus beads are primarily fluorescent in the vertically polarized channel, whereas FRET fluorescence was depolarized, and thus equally detected in both polarization channels (FIG. 4D). Use of a ratio approach to calculate the anisotropy of each bead (FIG. 4E) allows discrimination of FRET from no FRET even for weak signals (compare Venus beads in FIGS. 4C, 4E). Thus AFRET provides a robust method to discriminate FRET from no FRET conditions.

Adaptation of A-FRET assays to a high throughput approach was tested using a novel laser scanning fluorimeter capable of simultaneously measuring both Cerulean (FIGS. 5A, 5B) and Venus polarized fluorescence (FIGS. 5C, 5D) (unpublished). The figures show laser scanning images of COS-7 cells transfected with those FP-constructs. FP-labeled beads were measured in both 384-well glass-bottom plates and 96-well polystyrene plates to verify the ability to measure anisotropy in polystyrene plates. While some depolarization was seen in the polystyrene plates, it was minimal compared to the differences in fluorescence anisotropy between the FRET and non-FRET samples. Accurate anisotropy values were obtained for FP-labeled beads (FIG. 5E), and a mixed population of beads was accurately separated into FRET and non-FRET categories by plotting yellow fluorescence anisotropy verses cyan fluorescence anisotropy (FIG. 2F). Extraction of object anisotropies in this manner permits a simplified data processing strategy, composed of first reducing images to objects, and then determining the intensity values for each object, and using these values to calculate the anisotropy. Accurate anisotropies were also obtained for FPs expressed in COS-7 cells (FIG. 5G), and the difference between anisotropy values in the cyan and yellow channels (FIG. 5H) was used as a robust internal referencing standard for determination of FRET on an object-by-object basis.

To test the ability of this approach to measure FRET changes in a live cell based assay, COS-7 cells were transfected with the apoptosis sensor, SCAT 3.1 (Nagai and Miyawaki, 2004), which consists of cyan and yellow FPs separated by a caspase-3 cleavage site (FIG. 6A). FRET occurs only in the intact SCAT 3.1, and induction of apoptosis leads to activation of caspase-3 protease, cleavage of the sensor, and reduction of FRET (FIGS. 6B, 6C). Consequently, emission in the yellow FP channel changes from highly depolarized fluorescence to highly polarized fluorescence (FIG. 6C, curves 2 and 4), following induction of apoptosis using staurosporine. SCAT 3.1 cleavage was also monitored in cells grown on a 96-well plate. Treatment with hydrogen peroxide resulted in a increase in the overall anisotropy of in the yellow emission channel (FIG. 6D), indicating caspase-3 activation. Overall, A-FRET is sensitive and robust method for discrimination of FP-FRET from non-FRET conditions. The use of an intrinsic parameter, such as anisotropy, enables absolute threshold values to be determined for occurrence of FRET during an assay. This makes the method generally free from false positive indications of FRET and simplifies data handling by permitting object oriented processing. Accordingly, A-FRET is exceptionally well suited for use in high throughput assays.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

VIII. References

The following references, to the extent that they provide exemplary procedural or other details supplementary to those set forth herein, are specifically incorporated herein by reference:

U.S. Pat. No. 4,659,774
U.S. Pat. No. 4,682,195
U.S. Pat. No. 4,683,202
U.S. Pat. No. 4,684,611
U.S. Pat. No. 4,816,571
U.S. Pat. No. 4,879,236
U.S. Pat. No. 4,952,500
U.S. Pat. No. 4,959,463
U.S. Pat. No. 5,141,813
U.S. Pat. No. 5,264,566
U.S. Pat. No. 5,302,523
U.S. Pat. No. 5,322,783
U.S. Pat. No. 5,384,253
U.S. Pat. No. 5,428,148
U.S. Pat. No. 5,464,765
U.S. Pat. No. 5,538,877
U.S. Pat. No. 5,538,880
U.S. Pat. No. 5,550,318
U.S. Pat. No. 5,554,744
U.S. Pat. No. 5,563,055
U.S. Pat. No. 5,574,146
U.S. Pat. No. 5,580,859
U.S. Pat. No. 5,589,466
U.S. Pat. No. 5,602,244
U.S. Pat. No. 5,610,042
U.S. Pat. No. 5,645,897
U.S. Pat. No. 5,656,610
U.S. Pat. No. 5,702,932
U.S. Pat. No. 5,705,629
U.S. Pat. No. 5,736,524
U.S. Pat. No. 5,780,448
U.S. Pat. No. 5,789,215
U.S. Pat. No. 5,871,986
U.S. Pat. No. 5,925,565
U.S. Pat. No. 5,928,906
U.S. Pat. No. 5,945,100
U.S. Pat. No. 5,981,274
U.S. Pat. No. 5,994,624
Almendro et al., *J. Immunol.*, 157(12):5411-5421, 1996.
Angel et al., *Mol. Cell. Biol.*, 7:2256, 1987a.
Angel et al., *Cell*, 49:729, 1987b.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1996.
Axelrod, *Biophys. J.*, 26:557-573, 1979.
Baculovirus Expression Vectors, A Laboratory Manual, and Current Protocols in Molecular Biology, Bio/Technology, 6, 47, 1988.

Banerji et al., *Cell*, 27(2 Pt 1):299-308, 1981.
Banerji et al., *Cell*, 33(3):729-740, 1983.
Bates, *Mol. Biotechnol.*, 2(2):135-145, 1994.
Battraw and Hall, *Theor. App. Genet.*, 82(2):161-168, 1991.
Berkhout et al., *Cell*, 59:273-282, 1989.
Bhattacharjee et al., *J. Plant Bioch. Biotech.*, 6(2):69-73, 1997.
Blackman et al., *Biophys. J.*, 71:194-208, 1996.
Blanar et al., *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269; 1989.
Bulla and Siddiqui, *J. Virol.*, 62:1437, 1986.
Campbell and Villarreal, *Mol. Cell. Biol.*, 8:1993, 1988.
Campbell et al., *Proc. Natl. Acad. Sci. USA*, 99(12), 2002.
Campere and Tilghman, *Genes and Dev.*, 3:537, 1989.
Campo et al., *Nature*, 303:77, 1983.
Capaldi et al., *Biochem. Biophys. Res. Comm.*, 74(2):425-433, 1977.
Carbonelli et al., *FEMS Microbiol. Lett.*, 177(1):75-82, 1999.
Celander and Haseltine, *J. Virology*, 61:269, 1987.
Celander et al., *J. Virology*, 62:1314, 1988.
Chandler et al., *Cell*, 33:489, 1983.
Chandler et al., *Proc. Natl. Acad. Sci. USA*, 94(8):3596-601, 1997.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell. Biol.*, 7(8):2745-2752, 1987.
Chiu et al., *Nat. Cell. Biol.*, 4(5):343-350, 2002.
Choi et al., *Cell*, 53:519, 1988.
Christou et al., *Proc. Natl. Acad. Sci. USA*, 84(12):3962-3966, 1987.
Clegg, *Methods Enzymol.* 211:353-388, 1992.
Clegg, *Methods Enzymol.*, 211:353-388, 1992.
Cocea, *Biotechniques*, 23(5):814-816, 1997.
Cohen et al., *J. Cell. Physiol.*, 5:75, 1987.
Costa et al., *Mol. Cell. Biol.*, 8:81, 1988.
Cripe et al., *EMBO J.*, 6:3745, 1987.
Cubitt et al., *Methods Cell Biol.*, 58:19-30, 1999.
Culotta and Hamer, *Mol. Cell. Biol.*, 9:1376, 1989.
Dandolo et al., *J. Virology*, 47:55-64, 1983.
De Villiers et al., *Nature*, 312(5991):242-246, 1984.
Deschamps et al., *Science*, 230:1174-1177, 1985.
D'Halluin et al., *Plant Cell*, 4(12):1495-1505, 1992.
Edbrooke et al., *Mol. Cell. Biol.*, 9:1908, 1989.
Edlund et al., *Science*, 230:912-916, 1985.
EPO 0273085
Fechheimer et al., *Proc. Natl. Acad. Sci. USA*, 84:8463-8467, 1987.
Feng and Holland, *Nature*, 334:6178, 1988.
Firak and Subramanian, *Mol. Cell. Biol.*, 6:3667, 1986.
Foecking and Hofstetter, *Gene*, 45(1):101-105, 1986.
Förster, *Ann. Phys.*, 6:54-75, 1948.
Förster, V., *Ann. Phys.*, 6:54, 1948.
Fraley et al., *Proc. Natl. Acad. Sci. USA*, 76:3348-3352, 1979.
Froehler et al., *Nucleic Acids Res.*, 14(13):5399-5407, 1986.
Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gilles et al., *Cell*, 33:717, 1983.
Gloss et al., *EMBO J.*, 6:3735, 1987.
Godbout et al., *Mol. Cell. Biol.*, 8:1169, 1988.
Goodbourn and Maniatis, *Proc. Natl. Acad. Sci. USA*, 85:1447, 1988.
Goodbourn et al., *Cell*, 45:601, 1986.
Gopal, *Mol. Cell. Biol.*, 5:1188-1190, 1985.
Graham and Van Der Eb, *Virology*, 52:456-467, 1973.
Greene et al., *Immunology Today*, 10:272, 1989
Griesbeck et al., *J. Biol. Chem.*, 276(31):29188-29194, 2001.
Griesbeck et al., *J. Biol. Chem.*, 276:29188-29194, 2001.
Grosschedl and Baltimore, *Cell*, 41:885, 1985.
Harland and Weintraub, *J. Cell Biol.*, 101:1094-1099, 1985.
Haslinger and Karin, *Proc. Natl. Acad. Sci. USA*, 82:8572, 1985.
Hauber and Cullen, *J. Virology*, 62:673, 1988.
He et al., *Plant Cell Reports*, 14 (2-3):192-196, 1994.
Heim et al., *Proc. Natl. Acad. Sci. USA*, 91(26):12501-1254, 1994.
Hen et al., *Nature*, 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Holbrook et al., *Virology*, 157:211, 1987.
Hong et al., *FEBS Lett.*, 400(2):233-237, 1997.
Horlick and Benfield, *Mol. Cell. Biol.*, 9:2396, 1989.
Hou and Lin, *Plant Physiology*, 111:166, 1996.
Huang et al., *Cell*, 27:245, 1981.
Hug et al., *Mol. Cell. Biol.*, 8:3065, 1988.
Hwang et al., *Mol. Cell. Biol.*, 10:585, 1990.
Hyun Bae et al., *J. Mol. Biol.*, 328:1071-1081, 2003.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Inouye and Inouye, *Nucleic Acids Res.*, 13: 3101-3109, 1985.
Jakobovits et al., *Mol. Cell. Biol.*, 8:2555, 1988.
Jameel and Siddiqui, *Mol. Cell. Biol.*, 6:710, 1986.
Jares-Erijman and Jovin, *Nat. Biotechnol.*, 21:1387-1395, 2003.
Jaynes et al., *Mol. Cell. Biol.*, 8:62, 1988.
Johnson et al., *Mol. Cell. Biol.*, 9:3393, 1989.
Kadesch and Berg, *Mol. Cell. Biol.*, 6:2593, 1986.
Kaeppler et al., *Plant Cell Reports*, 9:415-418, 1990.
Kaneda et al., *Science*, 243:375-378, 1989.
Karasawa et al., *Biochem J.*, 381:307-312, 2004.
Karin et al., *Mol. Cell. Biol.*, 7:606, 1987.
Katinka et al., *Cell*, 20:393, 1980.
Kato et al, *J. Biol. Chem.*, 266:3361-3364, 1991.
Kawamoto et al., *Mol. Cell. Biol.*, 8:267, 1988.
Kiledjian et al., *Mol. Cell. Biol.*, 8:145, 1988.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Kraus et al. *FEBS Lett.*, 428(3):165-170, 1998.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Lareyre et al., *J. Biol. Chem.*, 274(12):8282-8290, 1999.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lazzeri, *Methods Mol Biol*, 49:95-106, 1995.
Lee et al., *Biochem. Biophys. Res. Commun.*, 240(2):309-313, 1997.
Lee et al., *Environ. Mol. Mutagen.*, 13(1):54-59, 1989.
Lee et al., *Nature*, 294:228, 1981.

Lee et al., *Nucleic Acids Res.*, 12:4191-206, 1984.
Levenson et al., *Hum. Gene Ther.*, 9(8):1233-1236, 1998.
Levinson et al., *Nature*, 295:79, 1982.
Lin et al., *Mol. Cell. Biol.*, 10:850, 1990.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Majors and Varmus, *Proc. Natl. Acad. Sci. USA*, 80:5866, 1983.
Maniatis et al., Molecular Cloning, A Laboratory Manual, Cold Spring Harbor Press, Cold Spring Harbor, N.Y., 1990.
Mattheyses et al., *Biophys J.*, 87:2787-2797, 2004.
McNeall et al., *Gene*, 76:81, 1989.
Miksicek et al., *Cell*, 46:203, 1986.
Miyawaki et al., *Nature*, 388:882-887, 1997.
Miyawaki, *Dev. Cell.*, 4:295-305, 2003.
Mordacq and Linzer, *Genes and Dev.*, 3:760, 1989.
Moreau et al., *Nucl. Acids Res.*, 9:6047, 1981.
Muesing et al., *Cell*, 48:691, 1987.
Nabel et al., *Science*, 244(4910):1342-1344, 1989.
Nagai and Miyawaki, *Biochem. Biophys. Res. Commun.*, 319(1):72-77, 2004.
Nagai et al., *Nat. Biotechnol.*, 20(1):87-90, 2002.
Ng et al., *Nuc. Acids Res.*, 17:601, 1989.
Nicolau and Sene, *Biochim. Biophys. Acta*, 721:185-190, 1982.
Nicolau et al., *Methods Enzymol.*, 149:157-176, 1987.
Nomoto et al., *Gene*, 236(2):259-271, 1999.
Omirulleh et al., *Plant Mol. Biol.*, 21(3):415-28, 1993.
Ondek et al., *EMBO J.*, 6:1017, 1987.
Ormo et al., *Science*, 273(5280):1392-1395, 1996.
Ormo et al., *Science*, 273:1392-1395, 1996.
Ornitz et al., *Mol. Cell. Biol.*, 7:3466, 1987.
Palmiter et al., *Nature*, 300:611, 1982.
Patterson et al., *Anal. Biochem.*, 10:284, 2000.
Patterson et al., *Anal. Biochem.*, 284(2):438-440, 2000.
Patterson et al., *Anal. Biochem.*, 284:438-440, 2000.
Patterson et al., *J. Cell Sci.*, 114:837-838, 2001.
PCT Appln. WO 9217598
PCT Appln. WO 94/09699
PCT Appln. WO 95/06128
Pech et al., *Mol. Cell. Biol.*, 9:396, 1989.
Pelletier and Sonenberg, *Nature*, 334(6180):320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potrykus et al., *Mol. Gen. Genet.*, 199:183-188, 1985.
Potter et al., *Proc. Natl. Acad. Sci. USA*, 81:7161-7165, 1984.
Prasher et al., *Gene*, 111:229-233, 1992.
Queen and Baltimore, *Cell*, 35:741, 1983.
Quinn et al., *Mol. Cell. Biol.*, 9:4713, 1989.
Reddy et al., 9(22):1542-1550, 2002.
Redondo et al., *Science*, 247:1225, 1990.
Reid et al., *Biochemistry*, 36:6786-6791, 1997.
Reisman and Rotter, *Mol. Cell. Biol.*, 9:3571, 1989.
Resendez Jr. et al., *Mol. Cell. Biol.*, 8:4579, 1988.
Rhodes et al., *Methods Mol. Biol.*, 55:121-131, 1995.
Ripe et al., *Mol. Cell. Biol.*, 9:2224, 1989.
Rippe et al., *Mol. Cell. Biol.*, 10:689-695, 1990.
Rittling et al., *Nuc. Acids Res.*, 17:1619, 1989.
Rizzo and Piston, *Biophys.* 188:L14-16, 2005.
Rizzo et al., *J. Biol. Chem.*, 277:34168-34175, 2002.
Rizzo et al., *Nat. Biotechnol.*, 22(4):445-449, 2004.
Rocheleau et al., *Biophys. J.*, 84(6):4078-4086, 2003.
Rosen et al., *Cell*, 41:813, 1988.
Sakai et al., *Genes and Dev.*, 2:1144, 1988.
Sambrook et al., In: *Molecular cloning*, Cold Spring Harbor Laboratory Press, Cold Spring Harbor, N.Y., 2001.
Satakei et al., *J. Virology*, 62:970, 1988.
Schaffner et al., *J. Mol. Biol.*, 201:81, 1988.
Searle et al., *Mol. Cell. Biol.*, 5:1480, 1985.
Sekar and Periasamy, *J. Cell. Biol.*, 160:629-633, 2003.
Shagin et al., *Mol. Biol. Evol.*, 21(5):841-850, 2004.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem.* 1, 248:1, 1987.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Swedlow et al., *Proc. Natl. Acad. Sci. USA*, 99:2014-2019, 2002.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Thiesen et al., *J. Virology*, 62:614, 1988.
Ting et al., *Proc. Natl. Acad. Sci. USA*, 98:15003-15008, 2001.
Treisman, *Cell*, 42:889, 1985.
Tronche et al., *Mol. Biol. Med.*, 7:173, 1990.
Trudel and Constantini, *Genes and Dev.* 6:954, 1987.
Truong et al., *Nat. Struct. Biol.*, 8:1069-1073, 2001.
Tsien, *Ann. Rev. Biochem.*, 67:509-544, 1998.
Tsukada et al., *Plant Cell Physiol.*, 30(4)599-604, 1989.
Tsumaki et al., *J. Biol. Chem.*, 273(36):22861-22864, 1998.
Tur-Kaspa et al., *Mol. Cell. Biol.*, 6:716-718, 1986.
Tyndell et al., *Nuc. Acids. Res.*, 9:6231, 1981.
Vanderklish et al., *Proc. Natl. Acad. Sci. USA*, 97:2253-2258, 2000.
Vannice and Levinson, *J. Virology*, 62:1305, 1988.
Vasseur et al., *Proc Natl. Acad. Sci. U.S.A.*, 77:1068, 1980.
Wagner et al., *Proc. Natl. Acad. Sci. USA* 87(9):3410-3414, 1990.
Wang and Calame, *Cell*, 47:241, 1986.
Weber et al., *Cell*, 36:983, 1984.
Weinberger et al., *Mol. Cell. Biol.*, 8:988, 1984.
Wilson et al., *Science*, 244:1344-1346, 1989.
Winoto and Baltimore, *Cell* 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Wu et al., *Biochem. Biophys. Res. Commun.*, 233(1):221-6, 1997.
Yang et al., *Proc. Natl. Acad. Sci. USA*, 87:9568-9572, 1990.
Youvan et al., *Biotechnology et alia.*, 3:1-18, 1997.
Yutzey et al., *Mol. Cell. Biol.*, 9:1397, 1989.
Zacharias et al., *Science*, 296(5569):913-916, 2002.
Zhang et al., *Nat. Rev. Mol. Cell. Biol.*, 3:906-918, 2002.

Zhang et al., *Proc. Natl. Acad. Sci. USA*, 98:14997-15002, 2001.

Zhao-Emonet et al., *Biochim. Biophys. Acta*, 1442(2-3):109-119, 1998.

Zhou et al., *Exp. Hematol*, 21:928-933, 1993.

What is claimed is:

1. A method of detecting Förster resonance energy transfer comprising:
   (a) applying polarized light to a molecule comprising a donor fluorescent moiety and an acceptor fluorescent moiety molecule, wherein said acceptor fluorescent moiety is distinct from said donor fluorescent moiety; and
   (b) determining depolarization of emitted light from said acceptor fluorescent moiety,
wherein the amount of depolarized light is directly related to the amount of energy transfer between said acceptor and donor fluorescent moieties, and wherein said molecule is subjected to a test condition, and the amount of depolarized light is compared to that observed in the absence of said test condition.

2. The method of claim 1, wherein said molecule is a protein, a lipid, a carbohydrate or a nucleic acid.

3. The method of claim 1, wherein said molecule is a protein and said test condition is a folding state condition or a proteolytic cleavage.

4. The method of claim 1, wherein said molecule is a glycoprotein and said test condition is a folding state condition or a glycosylation event.

5. The method of claim 1, wherein said molecule is lipid and said test condition is a lipid cleavage event.

6. The method of claim 1, wherein said molecule is a nucleic acid and said test condition is a hybridization condition or a nucleolytic event.

7. The method of claim 1, wherein said molecule is an autocatalytic protein or nucleic acid.

8. The method of claim 1, wherein both polarized and depolarized emitted light from said acceptor fluorescent moiety is measured.

9. The method of claim 8, wherein polarized emitted light is caused by the fluorescence of the donor fluorescent moiety and fluorescence of the acceptor fluorescent moiety, and wherein polarized fluorescence of the acceptor fluorescence moiety results from direct excitation of the acceptor fluorescence moiety.

10. The method of claim 1, wherein said donor fluorescent moiety exhibits a polarized steady-state fluorescence.

11. The method of claim 2, wherein said donor fluorescent moiety is a protein, or is a molecule rigidly attached to a protein.

* * * * *

UNITED STATES PATENT AND TRADEMARK OFFICE
CERTIFICATE OF CORRECTION

PATENT NO. : 8,031,338 B2  Page 1 of 1
APPLICATION NO. : 11/291111
DATED : October 4, 2011
INVENTOR(S) : David Piston et al.

It is certified that error appears in the above-identified patent and that said Letters Patent is hereby corrected as shown below:

In column 1, lines 9-13, delete paragraph and insert --This invention was made with government support under grant nos. DK053434 and GM072048 awarded by the National Institutes of Health, grant no. BBI-9871063 awarded by the National Science Foundation, and grant no. FA9550-04-1-0455 awarded by the Department of Defense. The government has certain rights in the invention.-- therefor.

Signed and Sealed this
Thirtieth Day of October, 2012

David J. Kappos
*Director of the United States Patent and Trademark Office*

UNITED STATES PATENT AND TRADEMARK OFFICE
CERTIFICATE OF CORRECTION

PATENT NO. : 8,031,338 B2
APPLICATION NO. : 11/291111
DATED : October 4, 2011
INVENTOR(S) : David Piston et al.

It is certified that error appears in the above-identified patent and that said Letters Patent is hereby corrected as shown below:

In column 36, line 25, insert claims 12-20:
--12. The method of claim 11, wherein said fluorescent protein is selected from green fluorescent protein (GFP), blue fluorescent protein (BFP), cyan fluorescent protein (CFP), yellow fluorescent protein (YFP), enhanced green fluorescent protein (EGFP), enhanced yellow fluorescent protein (EYFP), orange fluorescent protein (OFP), red fluorescent protein (RFP), far red fluorescent protein (FRFP), Venus, Citrine, phiYFP, copGFP coral green fluorescent protein (CGFP), enhanced cyan fluorescent protein (ECFP), Cerulean, CyPet, T-Sapphire, Emerald, YPet, AcGFP1, AmCyan, AsRed2, dsRed, dsRed2, dsRed-Express, enhanced blue fluorescent protein (EBFP), HcRed, ZsGreen, ZsYellow, J-Red, TurboGFP, Kusabira Orange, Midoriishi Cyan, mOrange, DsRed-monomer, mStrawberry, mRFP1, tdTomato, mCherry, mPlum, and mRaspberry.
13. The method of claim 12, wherein said BFP protein is a protein with a peak emission wavelength less than 450 nm.
14. The method of claim 12, wherein said CFP protein is a protein with a peak emission wavelength in the range of 450 nm to 480 nm.
15. The method of claim 12, wherein said GFP protein is a protein with a peak emission wavelength in the range of 480 nm to 520 nm.
16. The method of claim 12, wherein said YFP protein is a protein with a peak emission wavelength in the range of 520 nm to 550 nm.
17. The method of claim 12, wherein said OFP protein is a protein with a peak emission wavelength in the range of 550 nm to 575 nm.
18. The method of claim 12, wherein said RFP protein is a protein with a peak emission wavelength in the range of 575 nm to 600 nm.
19. The method of claim 12, wherein said FRFP protein is a protein with a peak emission wavelength of greater than 600 nm.
20. The method of claim 12, wherein said donor fluorescent protein is BFP, and said acceptor fluorescent moiety is CFP, wherein said donor fluorescent protein is BFP, and said acceptor fluorescent moiety is GFP, wherein said donor fluorescent protein is BFP, and said acceptor fluorescent moiety is YFP, wherein said donor fluorescent protein is BFP, and said acceptor fluorescent moiety is OFP, wherein said donor fluorescent protein is BFP, and said acceptor Signed and Sealed this
Twenty-ninth Day of January, 2013

David J. Kappos
*Director of the United States Patent and Trademark Office* fluorescent moiety is RFP, wherein said donor fluorescent protein is BFP, and said acceptor fluorescent moiety is FRFP, wherein said donor fluorescent protein is CFP, and said acceptor fluorescent moiety is GFP, wherein said donor fluorescent protein is CFP, and said acceptor fluorescent moiety is YFP, wherein said donor fluorescent protein is CFP, and said acceptor fluorescent moiety is OFP, wherein said donor fluorescent protein is CFP, and said acceptor fluorescent moiety is RFP, wherein said donor fluorescent protein is CFP, and said acceptor fluorescent moiety is FRFP, wherein said donor fluorescent protein is GFP, and said acceptor fluorescent moiety is YFP, wherein said donor fluorescent protein is GFP, and said acceptor fluorescent moiety is OFP, wherein said donor fluorescent protein is GFP, and said acceptor fluorescent moiety is RFP, wherein said donor fluorescent protein is GFP, and said acceptor fluorescent moiety is FRFP, wherein said donor fluorescent protein is YFP, and said acceptor fluorescent moiety is OFP, wherein said donor fluorescent protein is YFP, and said acceptor fluorescent moiety is RFP, wherein said donor fluorescent protein is YFP, and said acceptor fluorescent moiety is FRFP, wherein said donor fluorescent protein is OFP, and said acceptor fluorescent moiety is RFP, wherein said donor fluorescent protein is OFP, and said acceptor fluorescent moiety is FRFP, or wherein said donor fluorescent protein is RFP, and said acceptor fluorescent moiety is FRFP.--.

UNITED STATES PATENT AND TRADEMARK OFFICE
CERTIFICATE OF CORRECTION

PATENT NO. : 8,031,338 B2  Page 1 of 3
APPLICATION NO. : 11/291111
DATED : October 4, 2011
INVENTOR(S) : David Piston et al.

It is certified that error appears in the above-identified patent and that said Letters Patent is hereby corrected as shown below:

Delete the title page and substitute therefore the attached title page showing the corrected number of claims in patent.

In column 36, line 25, insert claims 12-20:
--12. The method of claim 11, wherein said fluorescent protein is selected from green fluorescent protein (GFP), blue fluorescent protein (BFP), cyan fluorescent protein (CFP), yellow fluorescent protein (YFP), enhanced green fluorescent protein (EGFP), enhanced yellow fluorescent protein (EYFP), orange fluorescent protein (OFP), red fluorescent protein (RFP), far red fluorescent protein (FRFP), Venus, Citrine, phiYFP, copGFP coral green fluorescent protein (CGFP), enhanced cyan fluorescent protein (ECFP), Cerulean, CyPet, T-Sapphire, Emerald, YPet, AcGFP1, AmCyan, AsRed2, dsRed, dsRed2, dsRed-Express, enhanced blue fluorescent protein (EBFP), HcRed, ZsGreen, ZsYellow, J-Red, TurboGFP, Kusabira Orange, Midoriishi Cyan, mOrange, DsRed-monomer, mStrawberry, mRFP1, tdTomato, mCherry, mPlum, and mRaspberry.
13. The method of claim 12, wherein said BFP protein is a protein with a peak emission wavelength less than 450 nm.
14. The method of claim 12, wherein said CFP protein is a protein with a peak emission wavelength in the range of 450 nm to 480 nm.
15. The method of claim 12, wherein said GFP protein is a protein with a peak emission wavelength in the range of 480 nm to 520 nm.
16. The method of claim 12, wherein said YFP protein is a protein with a peak emission wavelength in the range of 520 nm to 550 nm.
17. The method of claim 12, wherein said OFP protein is a protein with a peak emission wavelength in the range of 550 nm to 575 nm.
18. The method of claim 12, wherein said RFP protein is a protein with a peak emission wavelength in the range of 575 nm to 600 nm.
19. The method of claim 12, wherein said FRFP protein is a protein with a peak emission wavelength of greater than 600 nm.

This certificate supersedes the Certificate of Correction issued January 29, 2013.

Signed and Sealed this
Nineteenth Day of February, 2013

Teresa Stanek Rea
*Acting Director of the United States Patent and Trademark Office*

20. The method of claim 12, wherein said donor fluorescent protein is BFP, and said acceptor fluorescent moiety is CFP, wherein said donor fluorescent protein is BFP, and said acceptor fluorescent moiety is GFP, wherein said donor fluorescent protein is BFP, and said acceptor fluorescent moiety is YFP, wherein said donor fluorescent protein is BFP, and said acceptor fluorescent moiety is OFP, wherein said donor fluorescent protein is BFP, and said acceptor fluorescent moiety is RFP, wherein said donor fluorescent protein is BFP, and said acceptor fluorescent moiety is FRFP, wherein said donor fluorescent protein is CFP, and said acceptor fluorescent moiety is GFP, wherein said donor fluorescent protein is CFP, and said acceptor fluorescent moiety is YFP, wherein said donor fluorescent protein is CFP, and said acceptor fluorescent moiety is OFP, wherein said donor fluorescent protein is CFP, and said acceptor fluorescent moiety is RFP, wherein said donor fluorescent protein is CFP, and said acceptor fluorescent moiety is FRFP, wherein said donor fluorescent protein is GFP, and said acceptor fluorescent moiety is YFP, wherein said donor fluorescent protein is GFP, and said acceptor fluorescent moiety is OFP, wherein said donor fluorescent protein is GFP, and said acceptor fluorescent moiety is RFP, wherein said donor fluorescent protein is GFP, and said acceptor fluorescent moiety is FRFP, wherein said donor fluorescent protein is YFP, and said acceptor fluorescent moiety is OFP, wherein said donor fluorescent protein is YFP, and said acceptor fluorescent moiety is RFP, wherein said donor fluorescent protein is YFP, and said acceptor fluorescent moiety is FRFP, wherein said donor fluorescent protein is OFP, and said acceptor fluorescent moiety is RFP, wherein said donor fluorescent protein is OFP, and said acceptor fluorescent moiety is FRFP, or wherein said donor fluorescent protein is RFP, and said acceptor fluorescent moiety is FRFP.--.

(12) United States Patent
Piston et al.

(10) Patent No.: US 8,031,338 B2
(45) Date of Patent: Oct. 4, 2011

(54) MEASURING FORSTER RESONANCE ENERGY TRANSFER WITH POLARIZED AND DEPOLARIZED LIGHT

(75) Inventors: David Piston, Nashville, TN (US); Mark Rizzo, Nottingham, MD (US)

(73) Assignee: Vanderbilt University, Nashville, TN (US)

( * ) Notice: Subject to any disclaimer, the term of this patent is extended or adjusted under 35 U.S.C. 154(b) by 1676 days.

(21) Appl. No.: 11/291,111

(22) Filed: Nov. 30, 2005

(65) Prior Publication Data

US 2006/0160111 A1      Jul. 20, 2006

Related U.S. Application Data

(60) Provisional application No. 60/632,668, filed on Dec. 2, 2004.

(51) Int. Cl.
*G01J 3/447*    (2006.01)
(52) U.S. Cl. ........................................ 356/327
(58) Field of Classification Search ........................ None
See application file for complete search history.

(56) References Cited

U.S. PATENT DOCUMENTS

| | | | |
|---|---|---|---|
| 6,500,650 B1 * | 12/2002 | Stanton et al. | 435/91.1 |
| 6,803,201 B2 * | 10/2004 | Sorge et al. | 435/6 |
| 6,821,750 B2 * | 11/2004 | Hobbs et al. | 435/69.1 |
| 6,972,198 B2 * | 12/2005 | Craig et al. | 436/164 |
| 7,033,810 B2 * | 4/2006 | Tian et al. | 435/196 |
| 7,183,066 B2 * | 2/2007 | Fernandez-Salas et al. | 435/7.32 |
| 2002/0152479 A1 * | 10/2002 | Lehmann et al. | 800/3 |
| 2003/0003520 A1 * | 1/2003 | Shan et al. | 435/7.21 |
| 2003/0228703 A1 | 12/2003 | Hoppe et al. | 436/172 |
| 2005/0095174 A1 * | 5/2005 | Wolf | 422/82.08 |
| 2005/0227306 A1 * | 10/2005 | Fox et al. | 435/23 |
| 2006/0141531 A1 * | 6/2006 | Ebright et al. | 435/7.1 |
| 2009/0294691 A1 * | 12/2009 | Trinquet et al. | 250/459.1 |

FOREIGN PATENT DOCUMENTS

| | | |
|---|---|---|
| EP | 1571448 | 9/2005 |
| WO | WO 2004/053499 | 6/2004 |
| WO | WO 2005/026730 | 3/2005 |
| WO | WO 2006/010839 | 2/2006 |

OTHER PUBLICATIONS

Moens et al., "Detection of Tryptophan to Tryptophan Energy Transfer in Proteins", The Protein Journal, vol. 23, No. 1, Jan. 2004.*

Chiu et al., "Ras signalling on the endoplasmic reticulum and the golgi," *Nat. Cell. Biol.*, 4(5):343-350, 2002.

Jares-Erijman and Jovin, "Fret Imaging," *Nat. Biotechnol.*, 21:1387-1395, 2003.

Karasawa et al., "Cyan-emitting and orange emitting fluorescent proteins as a donor/acceptor pair for fluorescence resonance energy transfer," *Biochem J.*, 381:307-312, 2004.

Mattheyses et al., "Polarized fluorescence resonance energy transfer microscopy," Biophys J., 87:2787-2797, 2004.

Miyawaki, "Visualization of the spatial and temporal dynamics of intracellular signaling," *Dev. Cell.*, 4:295-305, 2003.

Nagai et al., "A variant of yellow fluorescent protein with fast and efficient maturation for cell-biological applications," *Nat. Biotechnol.*, 20(1):87-90, 2002.

Prasher et al., "Primary structure of the aequorea victoria green-fluorescent protein," *Gene*, 111:229-233, 1992.

Rizzo and Piston, "High-contrast imaging of fluorescent protein fret by fluorescence polarization microscopy," *J. Biophys.*, 88:L14-L16, 2005.

Rizzo et al., "An improved cyan fluorescent protein variant useful for fret," *Nat. Biotechnol.*, 22(4):445-449, 2004.

Tsien, "The green fluorescent protein," *Ann. Rev. Biochem.*, 67:509-544, 1998.

Zacharias et al. "Partitioning of lipid-modified monomeric gfps into membrane microdomains of live cells," *Science*, 296(5569):913-916, 2002.

Cohen-Kashi et al., "Fluorescence resonance energy transfers measurements on cell surfaces via fluorescence polarization," *Biophysical Journal*, 82:1395-1402, 2002.

Moens et al., "Detection of tryptophan to tryptophan energy transfer in proteins," *Protein Journal*, 23:79-83, 2004.

Jameson et al., "Intrinsic fluorescence of elongation factor Tu in its complexes with GDP and elongation factor Ts," *Biochemistry*, 26:3894-3901, 1987.

Jares-Erijman and Jovin, "FRET imaging," *Nature Biotech.*, 21:1387-95, 2003.

Mitra et al., "Fluorescence resonance energy transfer between blue-emitting and red-shifted excitation derivatives of the green fluorescent protein," *Gene*, 173:13-7, 1996.

Weber, "Fluorescence-polarization spectrum and electronic-energy transfer in tyrosine, tryptophan and related compounds," *Biochem. J.*, 75:335-345, 1960.

Weber, "Fluorescence-polarization spectrum and electronic-energy transfer in proteins," *Biochem. J.*, 75: 345-352, 1960.

* cited by examiner

*Primary Examiner* — Ann Lam

(74) *Attorney, Agent, or Firm* — Fulbright & Jaworski

(57) ABSTRACT

The present invention provides improved methods for assessing Förster resonance energy transfer using polarized light. Specifically, the methods rely on measuring depolarized light emitted by fluorescent acceptor molecules.

20 Claims, 5 Drawing Sheets